… [19] [11] Patent Number: 4,804,400

United States Patent
Moser et al.

[45] Date of Patent: Feb. 14, 1989

[54] N-PHENYL-MALEIMIDES AND HERBICIDAL AND PLANT GROWTH REGULATING METHODS OF USE THEREOF

[75] Inventors: Hans Moser, Magden, Switzerland; Georg Pissiotas, Lörrach, Fed. Rep. of Germany; Hans-Georg Brunner, Lausen, Switzerland; Beat Böhner, Binningen, Switzerland; Marcus Baumann, Basel, Switzerland

[73] Assignee: Ciba-Geigy Corporation, Ardsley, N.Y.

[21] Appl. No.: 92,793

[22] Filed: Sep. 3, 1987

[30] Foreign Application Priority Data

Sep. 12, 1986 [CH] Switzerland ............... 3664/86
Apr. 28, 1987 [CH] Switzerland ............... 1616/87

[51] Int. Cl.$^4$ ............ C07D 207/448; C07D 207/452; A01N 37/24
[52] U.S. Cl. ........................................ 71/95; 548/549; 548/545
[58] Field of Search ............... 548/549; 71/95

[56] References Cited

U.S. PATENT DOCUMENTS

| | | | |
|---|---|---|---|
| 2,262,262 | 11/1941 | Speer | 548/549 |
| 3,741,981 | 6/1983 | Fujinami et al. | 548/545 |
| 3,775,170 | 7/1973 | Fujinami et al. | 548/545 |
| 4,138,243 | 2/1979 | Böhner et al. | 71/94 |
| 4,220,655 | 9/1980 | Böhner et al. | 424/274 |

FOREIGN PATENT DOCUMENTS 0190755 8/1986 European Pat. Off. .

*Primary Examiner*—David B. Springer
*Attorney, Agent, or Firm*—Kevin T. Mansfield; Edward McC. Roberts

[57] ABSTRACT

Novel derivatives of N-phenylmaleic acid imide and N-phenylsuccinimide have good pre- and post-emergence selective herbicidal properties and they influence plant growth. The compounds correspond to the formula I

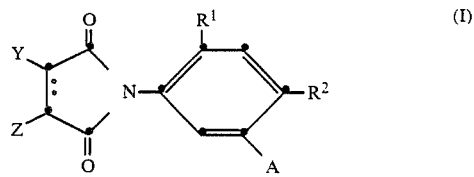

in which

| : represent a single or double bond,
$R^1$ represents hydrogen or fluorine,
$R^2$ represents halogen,
Y represents $C_1$-$C_8$-alkyl,
Z represents hydrogen or $C_1$-$C_8$-alkyl, and
A represents hydrogen or a group

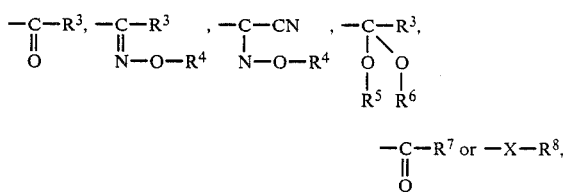

wherein
$R^3$, $R^4$, $R^5$, $R^6$, $R^7$ and $R^8$ represent customary organic radicals and X represents oxygen, sulphur, SO, $SO_2$, NH, alkylimino or alkenylimino.

18 Claims, No Drawings

N-PHENYL-MALEIMIDES AND HERBICIDAL AND PLANT GROWTH REGULATING METHODS OF USE THEREOF

The present invention relates to novel derivatives of N-phenyl-maleimide and N-phenyl-succinimide having a herbicidal and plant growth regulating action, to agrochemical compositions containing these substances as active ingredients, to the use of the novel N-phenyl-tetrahydrophthalimides for the selective control of weeds or for regulating plant growth, and to processes for the preparation of these novel compounds. The invention relates also to novel intermediates used for the preparation of the novel active ingredients.

The novel derivatives of N-phenylmaleimide and N-phenylsuccinimide correspond to the formula I

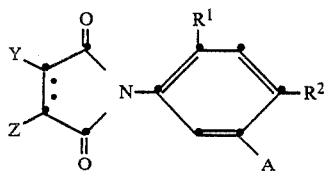

in which

|: represents a single or double bond,
$R^1$ represents hydrogen or fluorine,
$R^2$ represents halogen,
Y represents $C_1-C_8$-alkyl,
Z represents hydrogen or $C_1-C_8$-alkyl, and
A represents hydrogen or a group

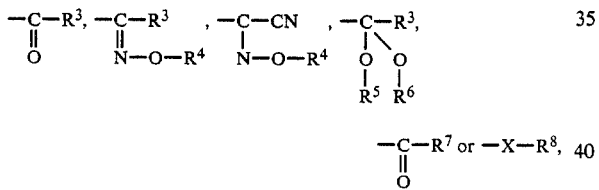

wherein $R^3$ represents hydrogen, $C_1-C_4$-alkyl or $C_1-C_4$-haloalkyl, $R^4$ represents hydrogen, $C_1-C_8$-alkyl, $C_2-C_8$-alkoxyalkyl, $C_2-C_8$-alkylthioalkyl, $C_2-C_8$-alkylaminoalkyl, $C_1-C_8$-haloalkyl, $C_1-C_8$-cyanoalkyl, $C_3-C_8$-alkenyl, $C_3-C_8$-haloalkenyl, $C_3-C_8$-alkynyl, $C_3-C_7$-cycloalkyl, $C_3-C_7$-halocycloalkyl, $C_1-C_4$-alkylsulphonyl, a sodium ion, a potassium ion, a magnesium ion, a calcium ion, an ammonium ion, $C_1-C_4$-alkoxycarbonyl, benzyloxycarbonyl, $C_5-C_7$-cycloalkoxycarbonyl, phenoxycarbonyl which is unsubstituted or mono-substituted at the phenyl ring by halogen, $C_1-C_4$-alkyl, $C_1-C_4$-alkoxy, $C_1-C_4$-haloalkyl, cyano or by nitro, or represents $C_1-C_4$-alkylthiocarbonyl, $C_1-C_4$-alkylaminocarbonyl, dimethylaminocarbonyl, benzylaminocarbonyl, $C_3-C_7$-cycloalkylaminocarbonyl, phenylaminocarbonyl which is unsubstituted or mono-substituted at the phenyl nucleus by halogen, $C_1-C_4$-alkyl, $C_1-C_4$-alkoxy, $C_1-C_4$-haloalkyl, cyano or by nitro, or represents $C_1-C_8$-alkylcarbonyl, allylcarbonyl, benzylcarbonyl which is unsubstituted or mono-substituted at the phenyl ring by halogen, $C_1-C_4$-alkyl, $C_1-C_4$-alkoxy, $C_1-C_4$-haloalkyl, cyano or by nitro, or represents $C_3-C_7$-cycloalkylcarbonyl, benzoyl which is unsubstituted or mono-substituted at the phenyl ring by halogen, $C_1-C_4$-alkyl, $C_1-C_4$-alkoxy, $C_1-C_4$-haloalkyl, cyano or by nitro, or represents furoyl or thenoyl; or represents $C_1-C_4$-alkyl substituted by phenyl, halophenyl, $C_1-C_4$-alkylphenyl, $C_1-C_4$-alkoxyphenyl, $C_1-C_4$-haloalkylphenyl, $C_1-C_4$-haloalkoxyphenyl, nitrophenyl, cyanophenyl, $C_1-C_8$-alkoxycarbonyl, $C_2-C_8$-alkoxyalkoxycarbonyl, $C_3-C_8$-alkenyloxycarbonyl, $C_3-C_8$-alkynyloxycarbonyl, $C_1-C_8$-alkylthiocarbonyl, $C_3-C_8$-alkenylthiocarbonyl, $C_3-C_8$-alkynylthiocarbonyl, carbamoyl, $C_1-C_4$-alkylaminocarbonyl, di-$C_1-C_4$-alkylaminocarbonyl, phenylaminocarbonyl which is unsubstituted or mono-substituted at the phenyl ring by halogen, $C_1-C_4$-alkyl, $C_1-C_4$-alkoxy, cyano, nitro or by $C_1-C_4$-haloalkyl; dioxolan-2-yl which is unsubstituted or substituted by one or two $C_1-C_4$-alkyl radicals; or 1,3-dioxan-2-yl which is unsubstituted or substituted by one or two $C_1-C_4$-alkyl radicals;

$R^5$ and $R^6$ represents, independently of the other, $C_1-C_4$-alkyl, $C_2-C_4$-haloalkyl or $C_2-C_8$-alkoxyalkyl, or $R^5$ and $R^6$ together represent an ethylene or propylene bridge or a 1,2-cyclohexanylene body, these groups being unsubstituted or substituted by one or two radicals selected from the group comprising $C_1-C_4$-alkyl, $C_1-C_4$-haloalkyl and $C_1-C_4$-hydroxyalkyl, $R^7$ represents hydroxy, $C_1-C_8$-alkoxy, $C_2-C_8$-alkoxyalkoxy, $C_2-C_8$-alkylthioalkoxy, $C_2-C_8$-alkylaminoalkoxy, $C_1-C_8$-cyanoalkoxy, $C_3-C_8$-alkenyloxy, $C_2-C_8$-haloalkenyloxy, $C_3-C_8$-alkynyloxy, $C_3-C_7$-cycloalkoxy, $C_3-C_7$-halocycloalkoxy, benzyloxy which is unsubstituted or mono-substituted at the phenyl nucleus by halogen, $C_1-C_4$-alkyl, $C_1-C_4$-alkoxy, $C_1-C_4$-haloalkyl, cyano or by nitro, or represents phenoxy, halophenoxy, $C_1-C_4$-alkylphenoxy, $C_1-C_4$-alkoxyphenoxy, $C_1-C_4$-haloalkylphenoxy, cyanophenoxy, nitrophenoxy, phenylthio, halophenylthio, $C_1-C_4$-alkylphenylthio, $C_1-C_4$-alkoxyphenylthio, $C_1-C_4$-haloalkylthio, cyanophenylthio, nitrophenylthio, the salt groups, —O—Na, —O—K, —O—Ca, —O—Mg, —O—NH$_4$; amino, $C_1-C_4$-alkylamino, di-$C_1-C_4$-alkylamino, $C_2-C_4$-haloalkylamino, di-$C_2-C_4$-haloalkylamino, $C_1-C_4$-hydroxyalkylamino, di-$C_1-C_4$-hydroxyalkylamino, $C_3-C_4$-alkenylamino, diallylamino, -N-pyrrolidino, -N-piperidino, -N-morpholino, -N-thiomorpholino, -N-piperidazino, $C_1-C_8$-alkylthio, $C_3-C_8$-alkenylthio, benzylthio, $C_1-C_4$-alkylthio substituted by $C_1-C_8$-alkoxycarbonyl, $C_2-C_8$-alkoxyalkoxycarbonyl, $C_3-C_8$-alkenyloxycarbonyl, $C_3-C_8$-alkynyloxycarbonyl, $C_1-C_8$-alkylthiocarbonyl, $C_3-C_8$-alkenylthiocarbonyl or by $C_3-C_8$-alkynylthiocarbonyl; or $C_1-C_4$-alkoxy substituted by $C_1-C_8$-alkoxycarbonyl, $C_2-C_8$-alkoxyalkoxycarbonyl, $C_3-C_8$-alkenyloxycarbonyl, $C_3-C_8$-alkynyloxycarbonyl, $C_1-C_8$-alkylthiocarbonyl, $C_3-C_8$-alkenylthiocarbonyl, $C_3-C_8$-alkynylthiocarbonyl, $C_1-C_4$-alkylaminocarbonyl, di-$C_1-C_4$-alkylaminocarbonyl or by phenylaminocarbonyl which is unsubstituted or mono-substituted at the phenyl nucleus by halogen, $C_1-C_4$-alkyl, $C_1-C_4$-alkoxy, $C_1-C_4$-haloalkyl, cyano or by nitro;

X represents oxygen, sulphur, —SO—, —SO$_2$—, —NH—, -N($C_1-C_4$-alkyl)- or -N($C_3-C_4$-alkenyl)-, and $R^8$ represents $C_1-C_8$-alkyl, $C_2-C_8$-alkoxyalkyl, $C_2-C_8$-alkylthioalkyl, $C_2-C_8$-alkylaminoalkyl, $C_2-C_8$-haloalkyl, $C_1-C_8$-cyanoalkyl, $C_3-C_8$-alkenyl, $C_2-C_8$- haloalkenyl, $C_3$–$C_8$-alkynyl, $C_3$–$C_7$-cycloalkyl, $C_3$–$C_7$-halocycloalkyl, $C_1$–$C_8$-alkylcarbonyl, allylcarbonyl, benzylcarbonyl which is unsubstituted or mono-substituted at the phenyl ring by halogen, $C_1$–$C_4$-alkyl, $C_1$–$C_4$-alkoxy, $C_1$–$C_4$-haloalkyl, cyano or by nitro, or represents $C_3$–$C_7$-cycloalkylcarbonyl, benzoyl which is unsubstituted or mono-substituted at the phenyl ring by halogen, $C_1$–$C_4$-alkyl, $C_1$–$C_4$-alkoxy, $C_1$–$C_4$-haloalkyl, cyano or by nitro, or represents furoyl or thienoyl, or $C_1$–$C_4$-alkyl substituted by phenyl, halophenyl, $C_1$–$C_4$-alkylphenyl, $C_1$–$C_4$-alkoxyphenyl, $C_1$–$C_4$-haloalkylphenyl, $C_1$–$C_4$-haloalkoxyphenyl, nitrophenyl, cyanophenyl, $C_1$–$C_8$-alkoxycarbonyl, $C_2$–$C_8$-alkoxyalkoxycarbonyl, $C_3$–$C_8$-alkenyloxycarbonyl, $C_3$–$C_8$-alkenylthiocarbonyl, $C_1$–$C_8$-alkylthiocarbonyl, $C_3$–$C_8$-alkenylthiocarbonyl, $C_3$–$C_8$-alkynylthiocarbonyl, carbamoyl, $C_1$–$C_4$-alkylaminocarbonyl, di-$C_1$–$C_4$-alkylaminocarbonyl, or by phenylaminocarbonyl which is unsubstituted or mono-substituted at the phenyl ring by halogen, $C_1$–$C_4$-alkyl, $C_1$–$C_4$-alkoxy, cyano, nitro or by $C_1$–$C_4$-haloalkyl; dioxolan-2-yl which is unsubstituted or substituted by one or two $C_1$–$C_4$-alkyl radicals; or 1,3-dioxan-2-yl which is unsubstituted or substituted by one or two $C_1$–$C_4$-alkyl radicals.

Derivatives of N-phenyl-2,3-dimethylmaleic acid imides are known as herbicides from the literature, from published Patent Applications DE-A No. 2 735 841 or JA-A No. 57.144 204 and from U.S. Pat. No. 4,138,243.

In the above definitions, the generic terms given include, for example, the following specific individual substituents, but this list does not constitute any limitation of the invention:

alkyl: methyl, ethyl, n-propyl, isopropyl, n-butyl, isobutyl, sec.-butyl and tert.-butyl, preferably methyl and ethyl.

halogen: fluorine, chlorine, bromine and iodine, preferably fluorine, chlorine and bromine.

alkoxy: methoxy, ethoxy, propoxy, isopropoxy, n-butoxy, isobutoxy, sec.-butoxy and tert.-butoxy, preferably methoxy or ethoxy.

haloalkyl: fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl, preferably chloromethyl, 2-chloroethyl and trifluoromethyl.

haloalkoxy: fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy, preferably difluoromethoxy, 2-chloroethoxy and trifluoromethoxy.

alkoxycarbonyl: methoxycarbonyl, ethoxycarbonyl, 4-propoxycarbonyl, isopropoxycarbonyl and n-butoxycarbonyl, preferably methoxycarbonyl and ethoxycarbonyl.

alkoxyalkyl: methoxymethyl, ethoxymethyl, propoxymethyl, methoxyethyl, ethoxyethyl, propoxyethyl, methoxypropyl, ethoxypropyl or propoxypropyl.

alkylthioalkyl: methylthiomethyl, ethylthiomethyl, methylthioethyl, ethylthioethyl or isopropylthioethyl.

alkylaminoalkyl: methylaminoethyl, dimethylaminoethyl, ethylaminoethyl or diethylaminoethyl.

cyanoalkyl: cyanomethyl, cyanoethyl or cyanopropyl.

alkenyl: allyl, 2-butenyl, 3-butenyl or methallyl, but preferably allyl.

alkynyl: propargyl, 2-butynyl or 3-butynyl, but preferably propargyl.

cycloalkyl: cyclopropyl, cyclobutyl, cyclopentyl, cyclohexyl or cycloheptyl. Cyclopentyl or cyclohexyl is preferred.

halocycloalkyl: 2,2-dichlorocyclopropyl or pentachlorocyclohexyl.

alkylsulphonyl: methylsulphonyl, ethylsulphonyl, propylsulphonyl or butylsulphonyl. Methyl- and ethylsulphonyl are preferred.

cycloalkoxycarbonyl: cyclopentyloxycarbonyl or cyclohexyloxycarbonyl.

phenyl, also as part of a larger substituent, such as phenoxy, phenylthio, phenoxycarbonyl, phenylaminocarbonyl, benzyl or benzoyl, may generally be unsubstituted or substituted by a further substituent. The substituents may then be in the ortho-, meta- or paraposition. Preferred substituent positions are the ortho- and para-position to the ring linking site. Preferred substituents are halogen atoms.

In the further substituents that are composed of several basic elements, the partial elements have the meanings explained above by reference to examples. These lists also do not represent in these cases any limitation of the invention: they are of an illustrative nature.

Among the compounds according to the invention these are preferred (a) the imides of the formula I in which
   $R^1$ represents hydrogen or fluorine,
   $R^2$ represents chlorine or bromine,
   Y represents $C_1$–$C_8$-alkyl,
   Z represents hydrogen or $C_1$–$C_8$-alkyl,
   A represents the radical —$COR^3$, and
   $R^3$ represents hydrogen, $C_1$–$C_4$-alkyl or $C_1$–$C_4$-haloalkyl;

(b) the imides of the formula I in which
   $R^1$ represents hydrogen or fluorine,
   $R^2$ represents chlorine or bromine,
   Y represents $C_1$–$C_8$-alkyl,
   Z represents hydrogen or $C_1$–$C_8$-alkyl,
   A represents the radical —$CR^3$=$NOR^4$, and
   $R^3$ and $R^4$ are as defined under formula I;

(c) the imides of the formula I in which
   $R^1$ represents hydrogen or fluorine,
   $R^2$ represents chlorine or bromine,
   Y represents $C_1$–$C_8$-alkyl,
   Z represents hydrogen or $C_1$–$C_8$-alkyl,
   A represents the radical —$C(CN)$=$NOR^4$, and
   $R^4$ is as defined under formula I;

(d) the imides of the formula I in which
   $R^1$ represents hydrogen or fluorine,
   $R^2$ represents chlorine or bromine,
   Y represents $C_1$–$C_8$-alkyl,
   Z represents hydrogen or $C_1$–$C_8$-alkyl,
   A represents the radical

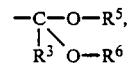

and
   $R^3$, $R^5$ and $R^6$ are as defined under formula I;

(e) the imides of the formula I in which
   $R^1$ represents hydrogen or fluorine,
   $R^2$ represents chlorine or bromine,
   Y represents $C_1$–$C_8$-alkyl,
   Z represents hydrogen or $C_1$–$C_8$-alkyl
   A represents the radical —$COR^7$, and
   $R^7$ is as defined under formula I;

(f) the imides of the formula I in which $R^1$ represents hydrogen or fluorine,
$R^2$ represents chlorine or bromine,
Y represents $C_1$-$C_8$-alkyl,
Z represents hydrogen or $C_1$-$C_8$-alkyl,
A represents the radical $-XR^8$, and
X and $R^8$ are as defined under formula I, specifically
N-(4-chloro-2-fluoro-5-isopropoxyphenyl)-2,3-dimethyl-maleic acid imide,
N-(4-chloro-2-fluoro-5-isopropoxyphenyl)-2-n-butyl-3-methyl-maleic acid imide and
N-(4-chloro-2-fluoro-5-isopropoxyphenyl)-2-ethyl-3-methyl maleic acid imide;

(g) the imides of the formula I in which
$R^1$ represents hydrogen or fluorine,
$R^2$ represents chlorine or bromine,
Y and Z each represents methyl, and
A has one of the meanings given under formula I;

(h) the imides of the formula I in which
$R^1$ represents hydrogen or fluorine,
$R^2$ represents chlorine or bromine,
Y represents ethyl,
Z represents methyl, and
A has one of the meanings given under formula I;

(i) the imides of the formula I in which
$R^1$ represents hydrogen or fluorine,
$R^2$ represents chlorine or bromine,
Y represents isopropyl,
Z represents methyl, and
A has one of the meanings given under formula I;

(k) the imides of the formula I in which
$R^1$ represents hydrogen or fluorine,
$R^2$ represents chlorine or bromine,
Y represents isopropyl,
Z represents hydrogen, and
A has one of the meanings given under formula I;

(l) the imides of the formula I in which
$R^1$ represents hydrogen or fluorine,
$R^2$ represents chlorine or bromine,
Y represents n-butyl,
Z represents methyl, and
A has one of the meanings given under formula I.

The compounds of the formula I are prepared according to the invention by condensing a maleic anhydride or a succinic anhydride of the formula II

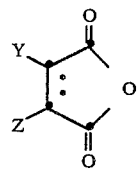
(II)

in which $|$: represents a single or double bond and Y and Z are as defined under formula I, with an aniline of the formula III

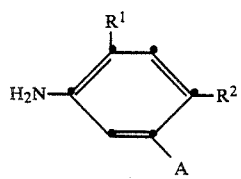
(III)

in which A, $R^1$ and $R^2$ are as defined under formula I.

The above condensation reaction is advantageously carried out in an inert organic solvent. The reaction temperature is generally between room temperature and the boiling temperature of the reaction mixture and, preferably, the reaction mixture is heated to the reflux. The condensation reaction can be accelerated by adding condensation catalysts and removing the water reaction product formed. The same effect is achieved by adding water-removing agents, such as, for example, sulphuric acid.

Suitable solvents are especially higher-boiling hydrocarbons, lower alkanecarboxylic acids and esters and amides thereof, higher-boiling ketones and ethers. Examples of these are benzene, toluene, xylene, dimethylformamide, dimethylacetamide, acetic acid, ethyl acetate, diisopropyl ether, ethylene glycol dimethyl ether, tetrahydrofuran, dioxan or 2-butanone.

Suitable catalysts, especially when a non-protic solvent is used, are: p-toluenesulphonic acid, benzoic acid, 4-dimethylaminopyridine, sulphuric acid, hydrochloric acid or naphthalenesulphonic acid. Reaction procedures of the type mentioned above are customarily used when preparing carboxylic acid derivatives. They correspond to generally customary laboratory practice.

The anhydrides of the formula II are known or can be prepared by processes analogous to known processes.

The aniline derivatives of the formula III are novel and were developed and prepared specifically for the synthesis of the compounds of the formula I. The present invention therefore also relates to them.

The compounds of the formula III are prepared by arranging in an appropriate sequence reaction steps that are known per se, such as etherification of a phenolic hydroxy function, nitration of a phenyl nucleus and reduction of the aromatic nitro group to form an aromatic amino group.

The reactions shown in the accompanying schemes 1 to 9 serve to illustrate such methods of preparing the novel compounds of the formula III. The substituents $R^1$ to $R^8$ are as defined under formula I.

Scheme 1:

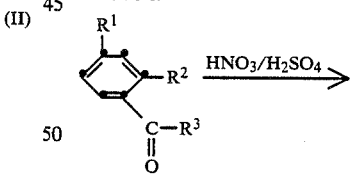

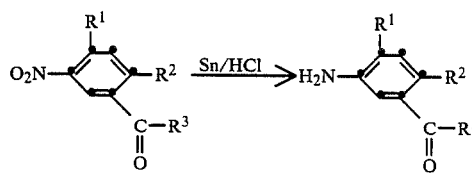

Scheme 2:

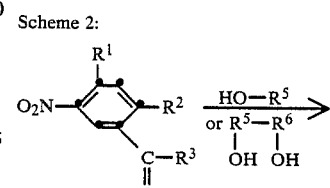

-continued
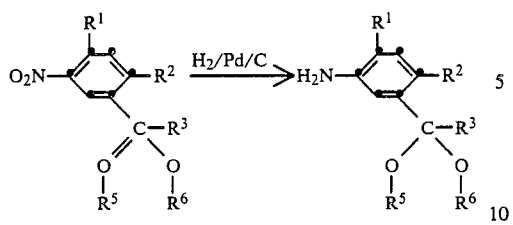
Scheme 6: Hal: chlorine, bromine
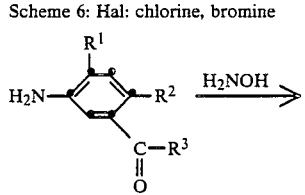
Scheme 3:
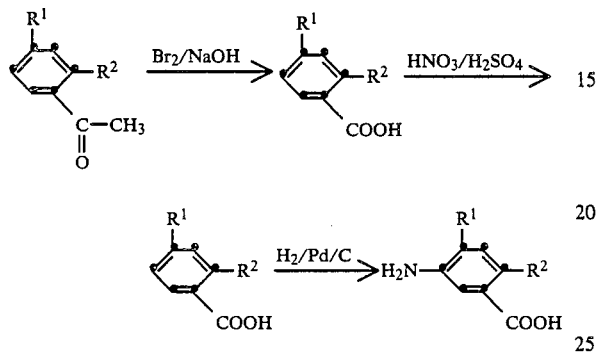
Scheme 4:
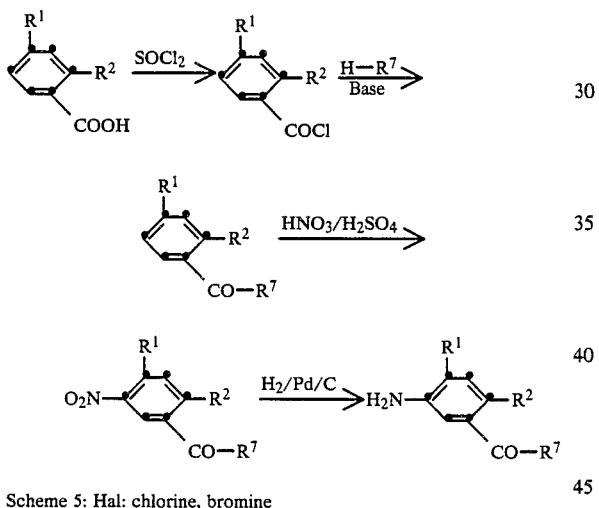
Scheme 5: Hal: chlorine, bromine
Scheme 7: Hal: chlorine, bromine; M⊕: Na⊕, K⊕
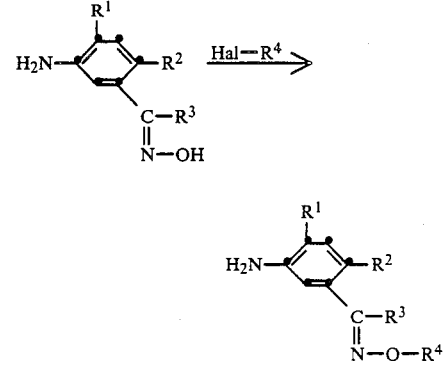
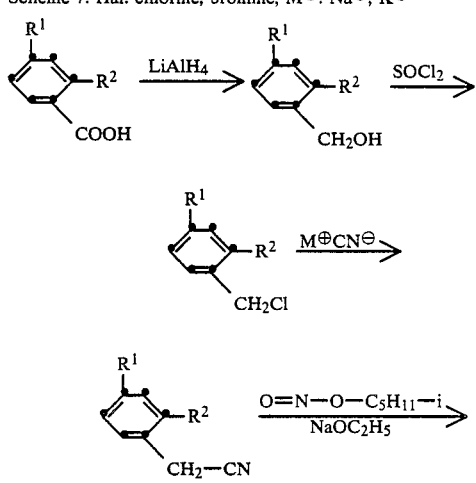
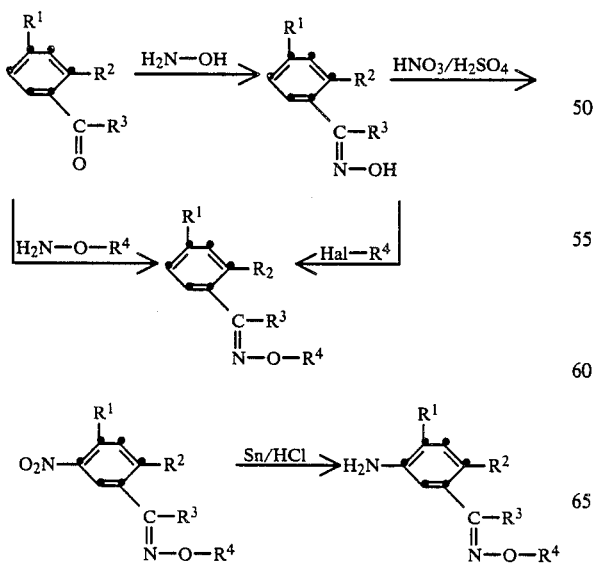
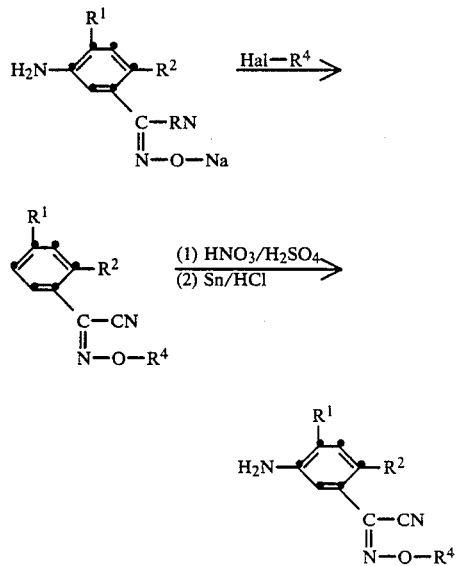

Scheme 8: Hal: chlorine, bromine

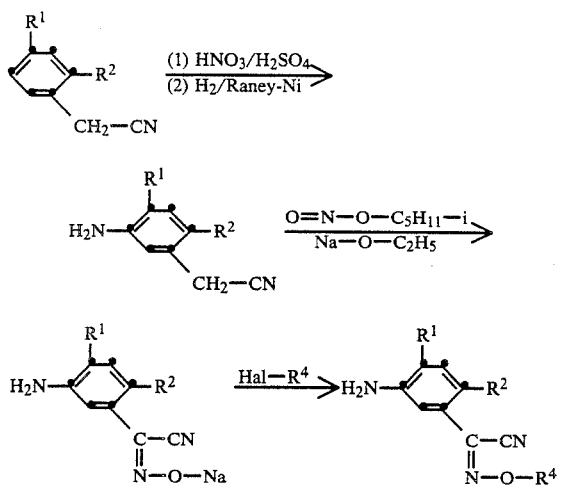

Scheme 9: Hal: chlorine, bromine

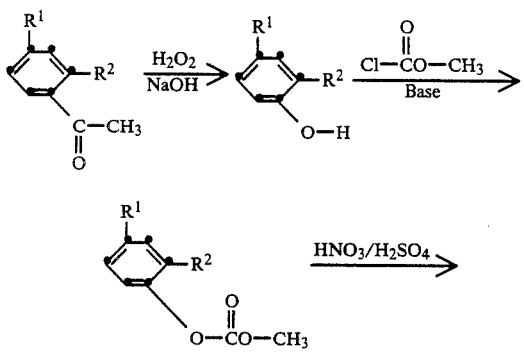

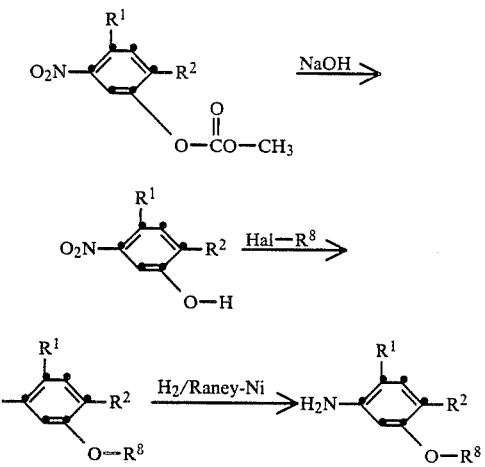

Although the synthesis of the compounds of the formula I from an anhydride of the formula II and an aniline of the formula III which is outlined above can be carried out in all cases, it may be wise from the point of view of economy or process technology to convert certain compounds of the formula I into other derivatives of the formula I. Suitable processes for such conversions are those that are known to a person skilled in the art, such as, for example, oxidation, reduction, esterification, hydrolysis or amidation. A few examples of such conversions of certain active ingredients of the formula I into other active ingredients of the formula I are listed in the following schemes 10 to 12.

Scheme 10:

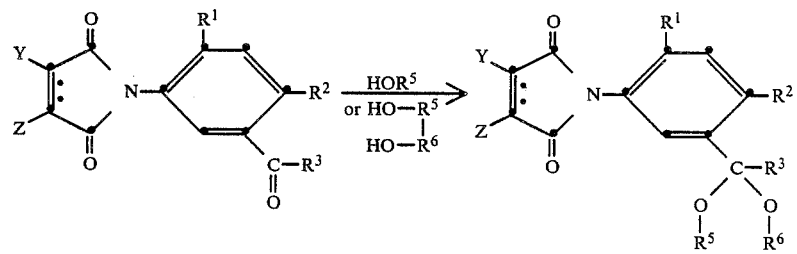

Scheme 11:

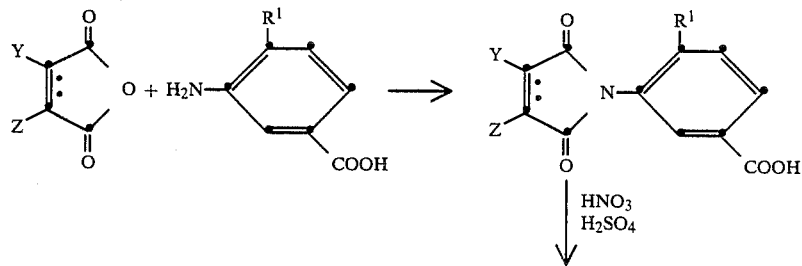

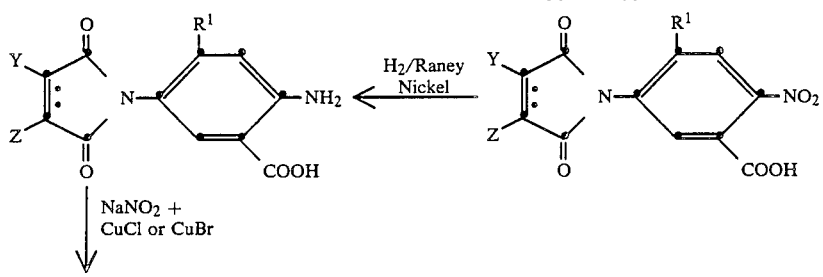

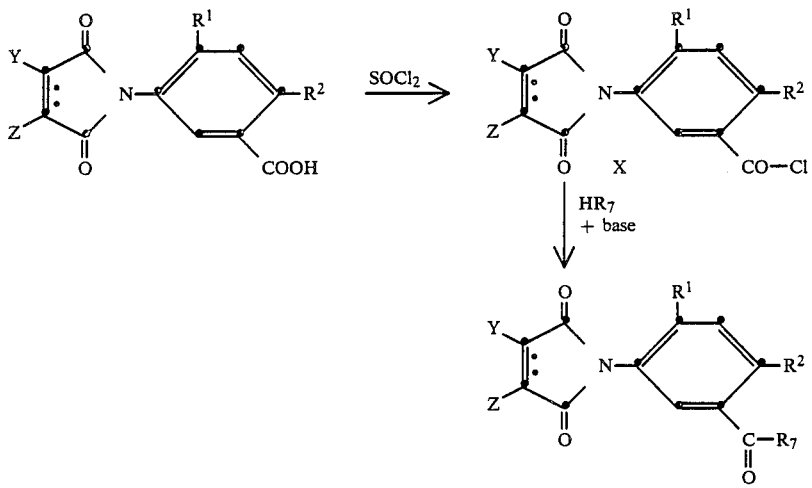

The acid chlorides of the formula X in which $R^1$ represents hydrogen or fluorine, $R^2$ represents chlorine or bromine, Y represents $C_1$-$C_8$-alkyl, and Z represents hydrogen or $C_1$-$C_8$-alkyl are important intermediates in the preparation of imides of the formula I. This invention relates also to them and to their preparation.

Scheme 12:
Hal: chlorine, bromine

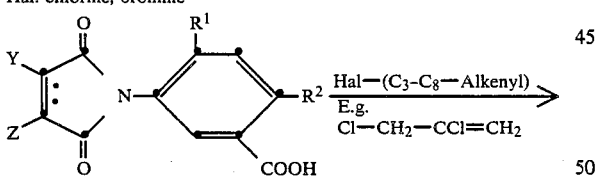

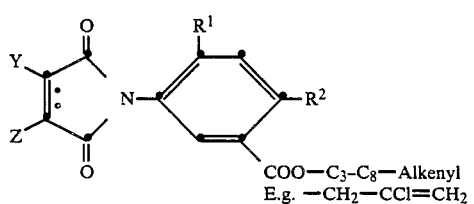

Scheme 13:

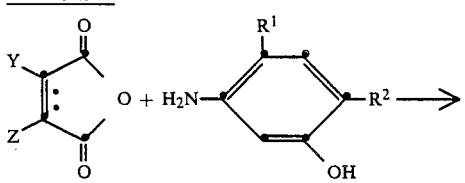

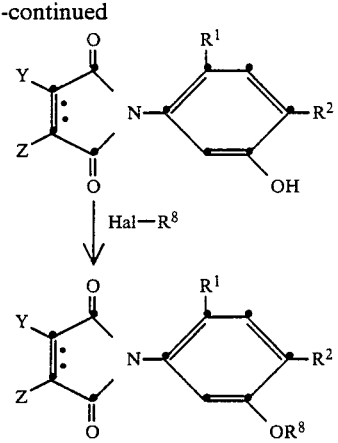

The active ingredients of the formula I according to the invention are stable compounds which do not require any particular precautions with regard to their handling.

If the succinimide compounds of the formula I are not synthesised directly from succinimides and phenyl compounds, they may be obtained also from the corresponding maleic derivatives. The conversion of the maleic acid imides into the corresponding succinimides is most advantageously effected by hydrogenating by means of hydrogen in the presence of a noble metal catalyst, such as, for example, platinum oxide. The hydrogenation can be carried out under normal pressure.

Depending on the position of the substituents Y and Z, the compounds of the formula I may occur in their E- or Z-form, i.e. the succinimides in their optical isomers and the maleinimides in their geometrical isomers. The radicals $R^3$, $R^4$, $R^7$ and $R^8$ may also contain asymmetric carbon atoms and compounds of the formula I containing such radicals may in turn be resolved into optically active isomers and/or be synthesized as such. This invention relates also to the stereoisomer compounds of the formula I.

The compounds of the formula I are highly active agrochemical active ingredients that, at suitable rates of application, are outstandingly suitable as selective herbicides for controlling weeds in crops of useful plants. That is to say, at those rates of application, the active ingredients of the formula I are distinguished by good selective herbicidal properties towards weeds. Crop plants such as rye, barley, oats, wheat, maize, millet, rice, cotton and soybeans remain virtually undamaged at low rates of application. When the rates of application are increased, the crop plants are only negligibly affected in their growth. If very high rates of application are used, the substances of the formula I exhibit total herbicidal properties.

The selective herbicidal action of the compounds according to the invention can be observed both when used pre-emergence and when used post-emergence. These active ingredients can therefore be used with equally good results both according to the pre-emergence method and according to the post-emergence method for selective weed control.

The invention relates also to herbicidal compositions that contain a novel active ingredient of the formula I, and to methods of controlling weeds pre-emergence and post-emergence.

The compounds of the formula I are used in unmodified form or, preferably, in the form of compositions together with the adjuvants conventionally employed in the art of formulation, and are therefore formulated in known manner into emulsifiable concentrates, directly sprayable or dilutable solutions, dilute emulsions, wettable powders, soluble powders, dusts, granulates, and also encapsulations in, for example, polymeric substances. As with the nature of the compositions, the methods of application, such as spraying, atomizing, dusting, scattering or pouring are chosen in accordance with the intended objectives and prevailing circumstances.

The formulations, i.e. the agents, preparations or compositions containing the active ingredient of the formula I and, where appropriate, a solid or liquid adjuvant, are prepared in known manner, for example by homogeneously mixing and/or grinding the active ingredients with extenders, such as, for example, solvents, solid carriers and, where appropriate, surface-active compounds (surfactants).

Suitable solvents are: aromatic hydrocarbons, preferably the fractions $C_8$ to $C_{12}$, such as, for example, xylene mixtures or substituted naphthalenes, phthalic acid esters such as dibutyl or dioctyl phthalate, aliphatic hydrocarbons such as cyclohexane or paraffins, alcohols and glycols and ethers and esters thereof, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, and also vegetable oils which may be epoxidised, such as epoxidised coconut oil or soybean oil; or water.

The solid carriers used, for example for dusts and dispersible powders, are normally powdered natural minerals, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types such as, for example, pumice, broken brick, sepiolite or bentonite; and suitable non-sorbent carriers are, for example, calcite or sand. In addition, a great number of pregranulated materials of inorganic or organic nature can be used, such as, especially, dolomite or pulverised plant residues.

Depending on the nature of the active ingredient of the formula I that is to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both so-called water-soluble soaps and water-soluble synthetic surface-active compounds.

Soaps that may be mentioned are the alkali metal salts, alkaline earth metal salts or unsubstituted or substituted ammonium salts of higher fatty acids ($C_{10}$–$C_{22}$), such as, for example, the sodium or potassium salts of oleic or stearic acid, or of natural fatty acid mixtures which can be obtained, for example, from coconut oil or tallow oil. Mention may also be made of fatty acid methyltaurin salts.

More frequently, however, so-called synthetic surfactants are used, especially fatty sulphonates, fatty sulphates, sulphonated benzimidazole derivatives or alkylarylsulphonates.

The fatty sulphonates or sulphates are, as a rule, in the form of alkali metal salts, alkaline earth metal salts or unsubstituted or substituted ammonium salts and contain an alkyl radical having from 8 to 22 carbon atoms, alkyl also including the alkyl moiety of acyl radicals, for example the sodium or calcium salt of lignosulphonic acid, of dodecylsulphate or of a mixture of fatty alcohol sulphates prepared from natural fatty acids.

These compounds also include the salts of sulphuric acid esters and sulphonic acids of fatty alcohol/ethylene oxide adducts. The sulphonated benzimidazole derivatives preferably contain 2 sulphonic acid groups and one fatty acid radical containing from 8 to 22 carbon atoms. Examples of alkylarylsulphonates are the sodium, calcium or triethanolamine salts of dodecylbenzenesulphonic acid, of dibutylnaphthalenesulphonic acid or of a naphthalenesulphonic acid/formaldehyde condensation product.

Also suitable are corresponding phosphates, such as, for example, salts of the phosphoric acid ester of an adduct of p-nonylphenol with from 4 to 14 moles of ethylene oxide, or phospholipids.

Non-ionic surfactants are especially polyglycol ether derivatives of aliphatic or cycloaliphatic alcohols, of saturated or unsaturated fatty acids and alkylphenols, which derivatives may contain from 3 to 10 glycol ether groups and from 8 to 20 carbon atoms in the (aliphatic) hydrocarbon moiety and from 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The compounds mentioned usually contain from 1 to 5 ethylene glycol units per propylene glycol unit.

Examples of non-ionic surfactants that may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan such as polyoxyethylene sorbitan trioleate are also suitable.

Cationic surfactants are especially quaternary ammonium salts that contain, as N-substituent, at least one alkyl radical having from 8 to 22 carbon atoms and, as further substituents, lower optionally halogenated alkyl, benzyl or lower hydroxyalkyl radicals. The salts are preferably in the form of halides, methyl sulphates or ethyl sulphates, for example stearyltrimethylammonium chloride or benzyldi(2-chloroethyl)ethylammonium bromide.

The surfactants customarily employed in the art of formulation are described, inter alia, in the following publications:

"McCutcheon's Detergent and Emulsifiers Annual" Publishing Corp., Ridgewood, N.J., 1981;

H. Stache, "Tensid-Taschenbuch", 2nd edition, C. Hanser Verlag, Munich, Vienna, 1981;

M. and J. Ash, "Encyclopedia of Surfactants", Vol. I–III, Chemical Publishing Co., New York, 1980–1981.

The herbicidal preparations usually contain from 0.1 to 95%, especially from 0.1 to 80%, active ingredient of the formula I, from 1 to 99.9% of a solid or liquid adjuvant and from 0 to 25%, especially from 0.1 to 25%, of a surfactant.

Preferred formulations have especially the following compositions (% = percent by weight):

| Emulsifiable concentrates: | |
|---|---|
| active ingredient: | 1 to 20%, preferably 5 to 10% |
| surfactants: | 5 to 30%, preferably 10 to 20% |
| liquid carriers: | 50 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 25%, preferably 88 to 30% |
| surfactant: | 1 to 40%, preferably 2 to 30% |
| Wettable powder: | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates: | |
| active ingredient: | 0.5 to 30%, preferably 3 to 15% |
| solid carrier: | 99.5 to 70%, preferably 97 to 85% |

Whereas concentrates are preferred as commercial products, the end user will as a rule use dilute formulations. The formulations can be diluted to a concentration as low as 0.001% active ingredient. The rates of application are normally from 0.001 to 4 kg active ingredient/ha, preferably from 0.005 to 1 kg active ingredient/ha.

The compositions may also contains further additives such as stabilisers, antifoams, viscosity regulators, binders, tackifiers and also fertilisers or other active ingredients for achieving special effects.

The following Examples illustrate the preparation of the imides of the formula I. Temperatures are given in degrees Celsius.

EXAMPLE 1

Preparation of N-(2-fluoro-5-carboxyphenyl)-2,3-dimethylmaleic acid imide (intermediate)

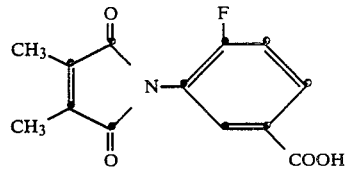

A mixture of 46.5 g of 3-amino-4-fluorobenzoic acid and 37.8 g of dimethylmaleic anhydride in 200 ml of glacial acetic acid is stirred for 12 hours at an oil bath temperature of 130°–40°. After cooling, the mixture is poured onto ice-water, and the resulting precipitate is filtered with suction, washed with water and dried. Recrystallisation from ethanol/water yields 70.3 g of N-(2-fluoro-5-carboxyphenyl)-2,3-dimethylmaleic acid imide which melts at 238°–240°.

EXAMPLE 2

Preparation of N-(2-fluoro-4-nitro-5-carboxyphenyl)-2,3-dimethylmaleic acid imide (intermediate)

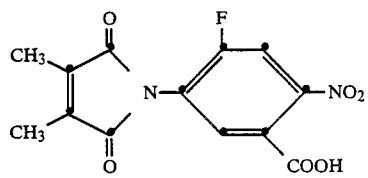

26.3 g of N-(2-fluoro-5-carboxyphenyl)-2,3-dimethylmaleic acid imide are introduced in portions, at 5°, into 230 ml of 96% sulphuric acid. There is then added dropwise to this mixture, while stirring vigorously at the same temperature, 5 ml of 100% nitric acid. The whole is further stirred overnight at room temperature and then poured into ice. The product which precipitates is filtered with suction, washed with water, dried and recrystallised from acetonitrile. 28 g of N-(2-fluoro-5-carboxy-4-nitrophenyl)-2,3-dimethylmaleic acid imide which has a melting point of 264°–265° is thus obtained.

EXAMPLE 3

Preparation of N-(2-fluoro-4-amino-5-carboxyphenyl)-2,3-dimethylmaleic acid imide (intermediate)

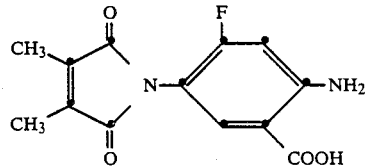

67.8 g of N-(2-fluoro-5-carboxy-4-nitrophenyl)-2,3-dimethylmaleic acid imide are hydrogenated using hydrogen in the presence of 14 g of Raney nickel catalyst in 1000 ml of tetrahydrofuran at a temperature of 20°–25° under normal pressure. When the stoichiometric amount of hydrogen has been consumed, the catalyst is separated off and the solution is concentrated by evaporation. 56.7 g of N-(2-fluoro-5-carboxy-4-aminophenyl)-2,3-dimethylmaleic acid imide having a melting point of 270° are thus obtained.

EXAMPLE 4

Preparation of N-(2-fluoro-4-chloro-5-carboxyphenyl)-2,3-dimethylmaleic acid imide

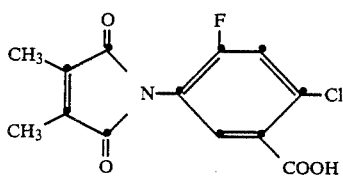

11.4 g of N-(2-fluoro-5-carboxy-4-aminophenyl)-2,3-dimethylmaleic acid imide are introduced in portions, at a temperature of 25°–30°, into 60 ml of glacial acetic acid and 60 ml of 96% sulphuric acid and the whole is stirred at that temperature for 1 hour. The solution is then stirred at 5° and an aqueous solution of 2.9 g of sodium nitrite in 17 ml of water is added dropwise thereto. The resulting diazo solution is added in portions, while stirring vigorously at 30°, to a solution of 4.5 g of copper(I) chloride in 32 ml of concentrated hydrochloric acid. When the evolution of nitrogen has ceased, the reaction mixture is heated at 60° for a further 30 minutes, while stirring, and then poured onto ice. The product which precipitates is filtered with suction, washed with water and recrystallised from methanol/water. 9.8 g of N-(2-fluoro-5-carboxy-4-chlorophenyl)-2,3-dimethylmaleic acid imide having a melting point of 230°–231° are obtained.

EXAMPLE 5

Preparation of N-(2-fluoro-4-chloro-5-chlorocarbonylphenyl)-2,3-dimethylmaleic acid imide (intermediate)

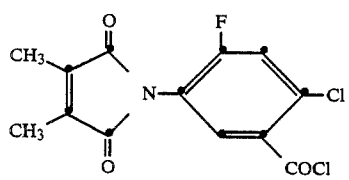

A mixture of 6 g of N-(2-fluoro-5-carboxy-4-chlorophenyl)-2,3-dimethylmaleic acid imide, 0.5 ml of dimethylmaleinimide, 2 ml of thionyl chloride and 50 ml of toluene is heated under reflux for 4 hours. After cooling, the whole is concentrated by evaporation in vacuo. 6 g of N-(2-fluoro-5-chlorocarbonyl-4-chlorophenyl)-2,3-dimethylmaleic acid imide having a melting point of 123°–124° are obtained.

EXAMPLE 6

Preparation of N-(2-fluoro-4-chloro-5-isopropoxycarbonylphenyl)-2,3-dimethylmaleic acid imide

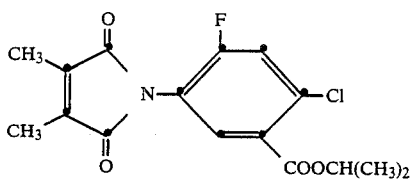

6 g of N-(2-fluoro-5-chlorocarbonyl-4-chlorophenyl)-2,3-dimethylmaleic acid imide are added dropwise, while stirring at room temperature, to a mixture of 4 ml of isopropanol, 4 ml of triethylamine and 100 ml of toluene. After a reaction time of 6 hours, the triethylamine hydrochloride is separated off by filtration and the filtrate is concentrated by evaporation. By recrystallising the residue from ethanol/water, 4.2 g of N-(2-fluoro-4-chloro-5-isopropoxycarbonylphenyl)-2,3-dimethylmaleic acid imide having a melting point of 161°–162° are obtained.

EXAMPLE 7

Preparation of N-[2-fluoro-4-chloro-5-(3-chlorallyloxycarbonyl)-phenyl]-2,3-maleic acid imide

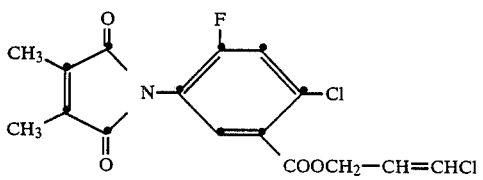

A mixture of 3 g of N-(2-fluoro-4-chloro-5-carboxyphenyl)-2,3-dimethylmaleic acid imide, 4.5 g of potassium carbonate, 1 ml of 1,3-dichloropropene and 50 ml of 2-butanone is heated under reflux for 16 hours. The precipitate is separated off and the filtrate is concentrated by evaporation. 3.3 g of N-[2-fluoro-5-(3-chlorallyloxycarbonyl)-4-chlorophenyl]-2,3-dimethylmaleic acid imide are obtained in the form of an oil. Refractive index $n_D^{24}$ 1.5640.

EXAMPLE 8

Preparation of N-(2-fluoro-5-methylcarbonylphenyl)-2,3-dimethylmaleic acid imide (intermediate)

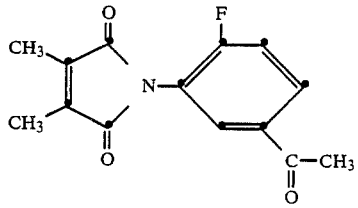

A mixture of 3 g of 5-amino-4-fluoroacetophenone, 2.5 g of dimethylmaleic anhydride and 50 ml of glacial acetic acid is heated under reflux overnight. The reaction mixture is then poured onto ice, and the resulting precipitate is filtered with suction, washed with water and dried. 2.3 g of N-(2-fluoro-5-methylcarbonyl-phenyl)-2,3-dimethylmaleic acid imide having a melting point of 130°–131° are thus obtained. By nitration, reduction and reaction with sodium nitrite and copper(I) chloride in accordance with Examples 2, 3 and 4 there can be obtained from this compound N-(2-fluoro-4-chloro-5-methylcarbonyl)-2,3-dimethylmaleic acid imide, m.p. 95°–97°.

EXAMPLE 9

Preparation of N-(2-fluoro-4-chlorophenyl)-2,3-dimethylmaleic acid imide

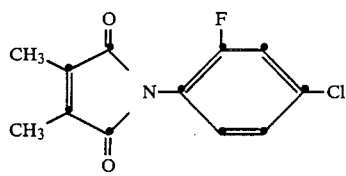

A mixture of 126 g (1.0 mol) of dimethylmaleic anhydride, 145.5 g (1.0 mol) of 2-fluoro-4-chloroaniline and 2 g of 4-dimethylaminopyridine is heated under reflux in 800 ml of o-xylene for 16 hours using a water separator. The whole is then evaporated to dryness in vacuo and the residue is dissolved in a 1:1 mixture of ethyl acetate:ether and washed with each of 1N hydrochloric acid, 1N sodium hydroxide solution and water. Afer drying over sodium sulphate and evaporating off the solvent, the residue (227.5 g) is recrystallised from methanol. In this manner there are obtained 211.1 g (84% of the theoretical yield) of the title product in the form of colourless crystals which melt at 96°–97°.

EXAMPLE 10

Preparation of N-(4-chloro-2-fluoro-5-isopropoxyphenyl)-2,3-dimethylmaleic acid imide

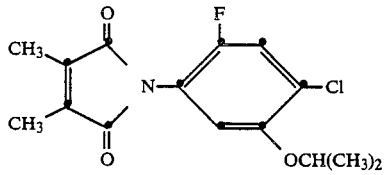

A mixture of 20.4 g (0.1 mol) of 2-fluoro-4-chloro-5-isopropoxyaniline and 12.6 g (0.1 mol) of dimethylmaleic anhydride in 100 ml of glacial acetic acid is stirred for 6 hours at a temperature of 130°–140°. It is then allowed to cool to room temperature and the almost black reaction solution is concentrated in a rotary evaporator. The residue is taken up in ethyl acetate and the solution is washed in succession with water, 1M soda solution, water and concentrated salt brine. It is then dried over sodium sulphate, filtered and concentrated in vacuo. The dark oil remaining is crystallised from ethanol with the aid of activated carbon. 17.6 g of title product (56.5% of the theoretical yield) which melts at 93°–95° is thus obtained.

EXAMPLE 11

Preparation of N-(2-fluoro-4-chlorophenyl)-2,3-dimethylsuccinimide

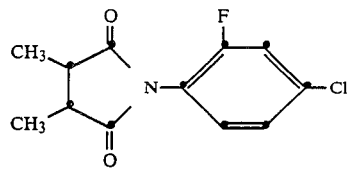

A mixture of 7.5 g (0.03 mol) of N-(4-chloro-2-fluoro-phenyl)-2,3-dimethylmaleic acid imide and 400 mg of platinum oxide (PtO$_2$) is hydrogenated with hydrogen in 75 ml of ethyl acetate at room temperature under normal pressure. After about 5 hours, the reduction is complete. The catalyst is then filtered off and the filtrate is concentrated in vacuo. 7.6 g (99% of the theoretical yield) of cis-N-(2-fluoro-4-chlorophenyl)-2,3-dimethyl-succinimide in the form of a yellowish oil which is uniform in a thin-layer chromatogram remain as residue.

$^1$H-NMR (300 MH$_2$, CDCl$_3$) 1.34 (d, 2xCH$_3$); 3.12 (m, CH—CH); 7.2 (m, 3 Ar. H).

EXAMPLE 12

Preparation of N-(2-fluoro-4-chloro-5-isopropoxyphenyl)-2,3-dimethyl-succinimide

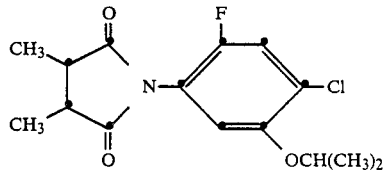

A mixture of 9.4 g (0.03 mol) of N-(2-fluoro-4-chloro-5-isopropoxyphenyl)-2,3-dimethylmaleic acid imide and 500 mg of platinum oxide (PtO$_2$) in 100 ml of ethyl acetate is hydrogenated with hydrogen at room temperature under normal pressure. After about 5 hours, when the absorption of hydrogen has ceased, the catalyst is filtered off and the filtrate is concentrated to dryness. 7.9 g (85% of the theoretical yield) of an almost colourless oil which is uniform in a thin-layer chromatogram are obtained as residue and crystallised from isopropyl ether. The cis-N-(2-fluoro-4-chloro-5-isopropoxyphenyl)-2,3-dimethyl-succinimide so obtained has a melting point of 101°–102°.

EXAMPLE 13

Preparation of N-(2-fluoro-4-chloro-5-isopropoxyphenyl)-2-ethyl-3-methylmaleic acid imide

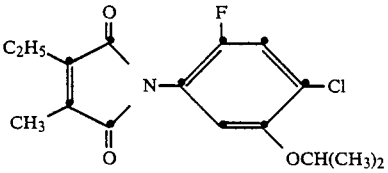

5 g of 2-ethyl-3-methylmaleic anhydride, 7.3 g of 2-fluoro-4-chloro-5-isopropoxyaniline and 0.61 g of 4-dimethylaminopyridine are combined in 100 ml of xylene in a distillation apparatus and the solvent is slowly distilled off. After 5 hours, the reaction is complete. The xylene still present is removed under a water-jet vacuum. The dark residue is taken up in ethyl acetate and extracted with 2M hydrochloric acid, water, 10% sodium bicarbonate solution and lastly with saturated sodium chloride solution. After drying over sodium sulphate, the ethyl acetate is distilled off in a rotary evaporator and the residue is chromatographed over a column of silica gel with hexane:ethyl acetate 1:1. After evaporating the solvent, 5 g of the title compound are obtained in the form of a red oil having a refractive index of $n_D^{22} = 1.5351$.

EXAMPLE 14

Preparation of N-(2-fluoro-4-chloro-5-hydroxyphenyl)-2,3-dimethyl-maleic acid imide

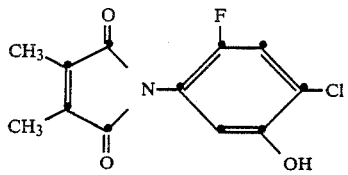

A mixture of 16.1 g of 2-fluoro-4-chloro-5-hydroxyaniline and 12.6 g of dimethylmaleic acid anhydride in 100 ml of propionic acid are heated to 150° and stirred for 12 hours at that temperature. The reaction mixture is then allowed to cool and concentrated. The residue is cristallized from methanol and yields 27.3 g of N-(2-fluoro-4-chloro-5-hydroxyphenyl)-2,3-dimethylmaleic acid imide melting at 170°–171°.

EXAMPLE 15

Preparation of N-(2-fluoro-4-chloro-5-propynyloxyphenyl)-2,3-dimethylmaleic acid imide.

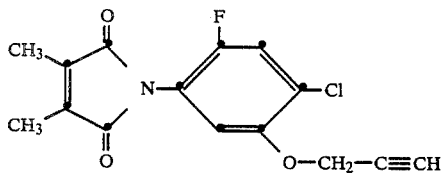

A mixture of 5.4 g of N-(2-fluoro-4-chloro-5-hydroxyphenyl)-2,3-dimethyl-maleic acid imide, 2.4 g of propynylbromide and 4 g of potassium carbonate in 100 ml of butan-2-on are heated to 100° and stirred for 2 hours at that temperature. The reaction mixture is then allowed to cool down, the precipitation is filtered off, and the filtrate is concentrated to dryness. After recrystallisation of the residue, 4.5 g of N-(2-fluoro-4-chloro-5-propynyloxyphenyl)2,3-dimethylmaleic acid anhydride is obtained, which melt at 149°–150°.

The compounds listed in the following Tables are prepared in a manner analogous to these Examples.

TABLE 1

| No. | $R^1$ | $R^2$ | A | |
|---|---|---|---|---|
| 1.01 | F | Cl | $COCH_3$ | |
| 1.02 | F | Cl | $COCH_2Cl$ | |
| 1.03 | F | Cl | $COCF_3$ | |
| 1.04 | F | | $COCH_3$ | |
| 1.05 | F | Cl | $C(CH_3)=N-OH$ | |
| 1.06 | F | Cl | $C(CH_3)=N-OCH_3$ | |
| 1.07 | F | Cl | $C(CN)=N-OH$ | |
| 1.08 | F | Br | $C(CN)=N-OC_2H_5$ | |
| 1.09 | F | Cl | $C(CN)=NOCH(CH_3)COOCH_3$ | |
| 1.10 | F | Cl | (cyclic carbonate-CH$_3$) | |
| 1.11 | F | Cl | (cyclic carbonate, CH$_3$, CH$_3$) | |
| 1.12 | F | Cl | (cyclic carbonate, CH$_2$Cl) | |
| 1.13 | F | Cl | COOH | m.p. 230–231° |
| 1.14 | F | Br | COOH | m.p. 231–233° |
| 1.15 | F | Cl | $COOCH_3$ | m.p. 137–138° |
| 1.16 | F | Cl | $COOCH(CH_3)_2$ | m.p. 101–102° |
| 1.17 | H | Cl | COOH | |
| 1.18 | H | Cl | $COOCH_3$ | |
| 1.19 | H | Cl | $COOCH(CH_3)_2$ | |
| 1.20 | F | Cl | $COSCH_2COOCH_3$ | m.p. 78–81° |
| 1.21 | F | Cl | $COSCH_2COOCH_2(CH_3)_2$ | |
| 1.22 | F | Cl | $COSCH(CH_3)COOCH_3$ | $n_D^{23}$ = 1.5668 |
| 1.23 | F | Cl | $COSCH(CH_3)COOCH_2CH=CH_2$ | |
| 1.24 | F | Cl | OH | m.p. 170–171° |
| 1.25 | F | Br | OH | |
| 1.26 | F | Cl | $OCH_3$ | |
| 1.27 | F | Cl | $OCH(CH_3)_2$ | m.p. 95–97° |
| 1.28 | F | Br | $OCH_2CH=CH_2$ | |
| 1.29 | F | Cl | $OCH_2CH=CHCl$ | |
| 1.30 | F | Cl | $OCH_2CCl=CH_2$ | |
| 1.31 | F | Cl | $OCH_2COOCH_3$ | |
| 1.32 | F | Cl | $OCH_2COOCH(CH_3)_2$ | |
| 1.33 | F | Cl | SH | |
| 1.34 | F | Br | SH | |
| 1.35 | F | Cl | $SCH_3$ | |
| 1.36 | F | Cl | $SCH(CH_3)_2$ | |
| 1.37 | F | Cl | $SCH_2CH=CHCl$ | |
| 1.38 | F | Cl | $SCH_2COOH$ | m.p. 165–167° |
| 1.39 | F | Br | $SCH_2COOH$ | |
| 1.40 | F | Cl | $SCH(CH_3)COOH$ | |
| 1.41 | F | Cl | $SCH_2COOCH_3$ | |
| 1.42 | F | Cl | $SCH(CH_3)COOCH_3$ | |
| 1.43 | F | Cl | $OCCl=CHCl$ | m.p. 127–130° |
| 1.44 | F | Cl | $OCF_3$ | m.p. 79–82° |
| 1.45 | F | Cl | $OCClF_2$ | m.p. 90–93° |
| 1.46 | F | H | COOH | m.p. 238–240° |
| 1.47 | H | Br | $COOCH(CH_3)_2$ | m.p. 93–95° |
| 1.48 | F | Br | $COOOCH(CH_3)_2$ | m.p. 104–105° |
| 1.49 | F | Br | $COSCH(CH_3)COOCH_3$ | m.p. 82–83° |

TABLE 1-continued

Structure: CH₃-C(=O)-C(=CH-...)-C(=O)-CH₃ connected via N to phenyl ring with R¹, R², A substituents

| No. | R¹ | R² | A | |
|---|---|---|---|---|
| 1.50 | F | Cl | COSCH(CH₃)COOC₂H₅ | $n_D^{23}$ = 1.5529 |
| 1.51 | F | Cl | COOCH₂CH(CH₃)₂ | m.p. 83–84° |
| 1.52 | F | Cl | COOC₂H₅ | m.p. 101–102° |
| 1.53 | F | Cl | COOCH(CH₃)COOCH₃ | $n_D^{23}$ = 1.5243 |
| 1.54 | F | Br | COOCH(CH₃)COOCH₃ | $n_D^{23}$ = 1.5398 |
| 1.55 | F | Br | COOCH(CH₃)CH₂SC₂H₅ | $n_D^{23}$ = 1,5301 |
| 1.56 | F | Br | COOCH(CH₃)CH₂SCH₃ | $n_D^{23}$ = 1,5670 |
| 1.57 | F | Br | COOCH(CH₃)CH₂SCH(CH₃)₂ | $n_D^{23}$ = 1,5271 |
| 1.58 | F | Br | COSCH(CH₃)COOC₂H₅ | $n_D^{23}$ = 1,5530 |
| 1.59 | F | Br | COSCH(CH₃)COOCH(CH₃)₂ | $n_D^{23}$ = 1,5252 |
| 1.60 | F | Cl | COOCH(CH₃)CH₂SC₂H₅ | $n_D^{23}$ = 1,5489 |
| 1.61 | F | Cl | COOCH₂CH=CHCl | $n_D^{24}$ = 1,5640 |
| 1.62 | F | Cl | COOCH(CH₃)COOC₂H₅ | $n_D^{24}$ = 1,5319 |
| 1.63 | F | Cl | COOCH(CH₃)CH₂SC(CH₃)₃ | $n_D^{23}$ = 1,5373 |
| 1.64 | F | Cl | COSCH(CH₃)COOCH(CH₃)₂ | $n_D^{23}$ = 1,5389 |
| 1.65 | F | Cl | COOCH₂CH=CH₂ | $n_D^{25}$ = 1,5532 |
| 1.66 | F | Cl | COSCH₂COOC₂H₅ | $n_D^{23}$ = 1,5639 |
| 1.67 | F | Cl | COOCH(CH₃)CH₂SCH₃H₇—n | $n_D^{25}$ = 1,5425 |
| 1.68 | F | Cl | COOCH(CH₃)CH₂SCH(CH₃)₂ | $n_D^{24}$ = 1,5432 |
| 1.69 | F | Cl | COOCH(C₃)CH₂SC₄H₉—n | $n_D^{25}$ = 1,5309 |
| 1.70 | F | H | COCH₃ | Smp. 130–131° |
| 1.71 | F | Cl | COOCH(CH₃)CH₂SCH₃ | $n_D^{25}$ = 1,5406 |
| 1.72 | F | Cl | OCH₂C≡CH | Smp. 149–150° |
| 1.73 | F | Cl | OCH(CH₃)COOCH₃ | Smp. 117–118° |
| 1.74 | F | Cl | —COOCH₂—C(Cl)=CH₂ | $n_D^{25}$ = 1,5422 |
| 1.75 | F | Cl | —COOCH₂—C(Br)=CH₂ | |
| 1.76 | F | Cl | —COO—CH₂—CH=CCl—CH₃ | |
| 1.77 | F | Cl | —COO—CH₂—C(Br)=CHBr | |
| 1.78 | F | Cl | —COOCH₂—C≡CH | |
| 1.79 | F | Br | —COOCH₂—CH=CCl.CH₃ | |
| 1.80 | F | Br | —COOCH₂—CCl=CH₂ | |
| 1.81 | F | Br | —COOCH₂—CH=CHCl | |
| 1.82 | F | Br | —COOCH₂—CBr=CH₂ | |
| 1.83 | F | Br | —O—CH₂—C≡CH | |
| 1.84 | F | Cl | —O—CH(CH₃)—CH₂—S—CH₃ | $n_D^{23}$ = 1,5468 |

TABLE 2

Structure: CH₃-CH(-C(=O)-...)-CH(CH₃)-C(=O)- with N-phenyl group bearing R¹, R², A

| No. | R¹ | R² | A |
|---|---|---|---|
| 2.01 | F | Cl | COCH₃ |
| 2.02 | F | Cl | COCH₂Cl |
| 2.03 | F | Cl | COCF₃ |
| 2.04 | F | | COCH₃ |
| 2.05 | F | Cl | C(CH₃)=N—OH |
| 2.06 | F | Cl | C(CH₃)=N—OCH₃ |
| 2.07 | F | Cl | C(CN)=N—OH |

TABLE 2-continued

| No. | R¹ | R² | A | |
|---|---|---|---|---|
| 2.08 | F | Br | C(CN)=N—OC₂H₅ | |
| 2.09 | F | Cl | C(CN)=NOCH(CH₃)COOCH₃ | |
| 2.10 | F | Cl | 2-methyl-1,3-dioxolan-2-yl (—C(CH₃)(O—)(O—) ring with CH₃) | |
| 2.11 | F | Cl | 2,2-dimethyl-1,3-dioxolan-yl (C with two O, CH₃ and CH₃) | |
| 2.12 | F | Cl | 2-(chloromethyl)-2-methyl-1,3-dioxolan-yl | |
| 2.13 | F | Cl | COOH | |
| 2.14 | F | Br | COOH | |
| 2.15 | F | Cl | COOCH₃ | |
| 2.16 | F | Cl | COOCH(CH₃)₂ | |
| 2.17 | H | Cl | COOH | |
| 2.18 | H | Cl | COOCH₃ | |
| 2.19 | H | Cl | COOCH(CH₃)₂ | |
| 2.20 | F | Cl | COSCH₂COOCH₃ | |
| 2.21 | F | Cl | COSCH₂COOCH(CH₃)₂ | |
| 2.22 | F | Cl | COSCH₂(CH₃)COOCH₃ | |
| 2.23 | F | Cl | COSCH(CH₃)COOCH₂CH=CH₂ | |
| 2.24 | F | Cl | OH | |
| 2.25 | F | Br | OH | |
| 2.26 | F | Cl | OCH₃ | |
| 2.27 | F | Cl | OCH(CH₃)₂ | m.p. 102° |
| 2.28 | F | Br | OCH₂CH=CH₂ | |
| 2.29 | F | Cl | OCH₂CH=CHCl | |
| 2.30 | F | Cl | OCH₂CCl=CH₂ | |
| 2.31 | F | Cl | OCH₂COOCH₃ | |
| 2.32 | F | Cl | OCH₂COOCH(CH₃)₂ | |
| 2.33 | F | Cl | SH | |
| 2.34 | F | Br | SH | |
| 2.35 | F | Cl | SCH₃ | |
| 2.36 | F | Cl | SCH(CH₃)₂ | |
| 2.37 | F | Cl | SCH₂CH=CHCl | |
| 2.38 | F | Cl | SCH₂COOH | |
| 2.39 | F | Br | SCH₂COOH | |
| 2.40 | F | Cl | SCH(CH₃)COOH | |
| 2.41 | F | Cl | SCH₂COOCH₃ | |
| 2.42 | F | Cl | SCH(CH₃)COOCH₃ | |
| 2.43 | F | Cl | H | oil |
| 2.44 | F | Cl | OCH₂C≡CH | |
| 2.45 | F | Cl | OCH(CH₃)COOCH₃ | |

TABLE 3

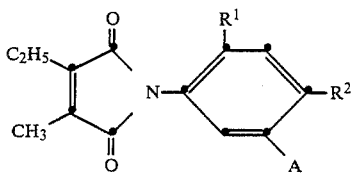

| No. | R¹ | R² | A |
|---|---|---|---|
| 3.01 | F | Cl | COCH$_3$ |
| 3.02 | F | Cl | COCH$_2$Cl |
| 3.03 | F | Cl | COCF$_3$ |
| 3.04 | F |  | COCH$_3$ |
| 3.05 | F | Cl | C(CH$_3$)=N—OH |
| 3.06 | F | Cl | C(CH$_3$)=N—OCH$_3$ |
| 3.07 | F | Cl | C(CN)=N—OH |
| 3.08 | F | Br | C(CN)=N—OC$_2$H$_5$ |
| 3.09 | F | Cl | C(CN)=NOCH(CH$_3$)COOCH$_3$ |
| 3.10 | F | Cl | (1,3-dioxolan-2-yl with 2-CH$_3$) |
| 3.11 | F | Cl | (1,3-dioxolan-2-yl with 2-CH$_3$, 4-CH$_3$) |
| 3.12 | F | Cl | (1,3-dioxolan-2-yl with 2-CH$_3$, 4-CH$_2$Cl) |
| 3.13 | F | Cl | COOH  m.p. 165° |
| 3.14 | F | Br | COOH |
| 3.15 | F | Cl | COOCH$_3$ |
| 3.16 | F | Cl | COOCH(CH$_3$)$_2$  m.p. 68–69° |
| 3.17 | H | Cl | COOH |
| 3.18 | H | Cl | COOCH$_3$ |
| 3.19 | H | Cl | COOCH(CH$_3$)$_2$  n$_D^{22}$ = 1.5458 |
| 3.20 | F | Cl | COSCH$_2$COOCH$_3$ |
| 3.21 | F | Cl | COSCH$_2$COOCH$_2$(CH$_3$)$_2$ |
| 3.22 | F | Cl | COSCH(CH$_3$)COOCH$_3$ |
| 3.23 | F | Cl | COSCH(CH$_3$)COOCH$_2$CH=CH$_2$ |
| 3.24 | F | Cl | OH  m.p. 74–75° |
| 3.25 | F | Br | OH |
| 3.26 | F | Cl | OCH$_3$ |
| 3.27 | F | Cl | OCH(CH$_3$)$_2$  n$_D^{22}$ = 1,5351 |
| 3.28 | F | Br | OCH$_2$CH=CH$_2$ |
| 3.29 | F | Cl | OCH$_2$CH=CHCl  n$_D^{23}$ = 1,5572 |
| 3.30 | F | Cl | OCH$_2$CCl=CH$_2$ |
| 3.31 | F | Cl | OCH$_2$COOCH$_3$ |
| 3.32 | F | Cl | OCH$_2$COOCH(CH$_3$)$_2$ |
| 3.33 | F | Cl | SH |
| 3.34 | F | Br | SH |
| 3.35 | F | Cl | SCH$_3$ |
| 3.36 | F | Cl | SCH(CH$_3$)$_2$ |
| 3.37 | F | Cl | SCH$_2$CH=CHCl |
| 3.38 | F | Cl | SCH$_2$COOH |
| 3.39 | F | Br | SCH$_2$COOH |
| 3.40 | F | Cl | SCH(CH$_3$)COOH |
| 3.41 | F | Cl | SCH$_2$COOCH$_3$ |
| 3.42 | F | Cl | SCH(CH$_3$)COOCH$_3$ |
| 3.43 | F | Cl | OCH$_2$C≡CH  m.p. 98–99° |
| 3.44 | F | Cl | OCH(CH$_3$)COOCH$_3$  n$_D^{24}$ = 1,5308 |
| 3.45 | F | Cl | COOCH(CH$_3$)—CH$_2$—S—CH$_3$ |
| 3.46 | F | Cl | COOCH(CH$_3$)—CH$_2$—S—C$_2$H$_5$ |
| 3.47 | F | Cl | COO—CH$_2$—CCl=CH$_2$ |
| 3.48 | F | Cl | COOCH$_2$—CH=CHCl |
| 3.49 | F | Cl | COOCH$_2$—CH=CCl—CH$_3$ |

TABLE 3-continued

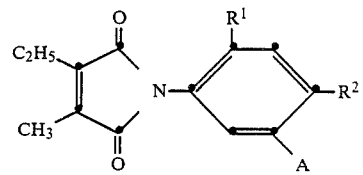

| No. | R¹ | R² | A |
|---|---|---|---|
| 3.50 | F | Cl | COOCH$_2$—CBr=CH$_2$ |
| 3.60 | F | Cl | COOCH$_2$—CH=CHBr |
| 3.61 | F | Br | COOCH$_2$—CCl=CH$_2$ |
| 3.62 | F | Br | COOCH$_2$—CH=CHCl |
| 3.63 | F | Br | COOCH$_2$—CH=CCl—CH$_3$ |
| 3.64 | F | Br | COOCH$_2$—CBr=CH$_2$ |
| 3.65 | F | Br | —O—CH$_2$—C≡CH |
| 3.66 | F | Br | —O—CH(CH$_3$)—COOCH$_3$ |

TABLE 4

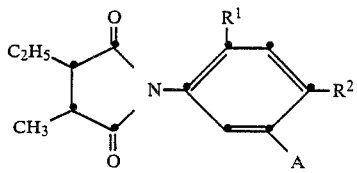

| No. | R¹ | R² | A |
|---|---|---|---|
| 4.01 | F | Cl | COCH$_3$ |
| 4.02 | F | Cl | COCH$_2$Cl |
| 4.03 | F | Cl | COCF$_3$ |
| 4.04 | F |  | COCH$_3$ |
| 4.05 | F | Cl | C(CH$_3$)=N—OH |
| 4.06 | F | Cl | C(CH$_3$)=N—OCH$_3$ |
| 4.07 | F | Cl | C(CN)=N—OH |
| 4.08 | F | Br | C(CN)=N—OC$_2$H$_5$ |
| 4.09 | F | Cl | C(CN)=NOCH(CH$_3$)COOCH$_3$ |
| 4.10 | F | Cl | (1,3-dioxolan-2-yl with 2-CH$_3$) |
| 4.11 | F | Cl | (1,3-dioxolan-2-yl with 2-CH$_3$, 4-CH$_3$) |
| 4.12 | F | Cl | (1,3-dioxolan-2-yl with 2-CH$_3$, 4-CH$_2$Cl) |
| 4.13 | F | Cl | COOH |
| 4.14 | F | Br | COOH |
| 4.15 | F | Cl | COOCH$_3$ |
| 4.16 | F | Cl | COOCH(CH$_3$)$_2$ |
| 4.17 | H | Cl | COOH |
| 4.18 | H | Cl | COOCH$_3$ |
| 4.19 | H | Cl | COOCH(CH$_3$)$_2$ |
| 4.20 | F | Cl | COSCH$_2$COOCH$_3$ |
| 4.21 | F | Cl | COSCH$_2$COOCH$_2$(CH$_3$)$_2$ |
| 4.22 | F | Cl | COSCH(CH$_3$)COOCH$_3$ |
| 4.23 | F | Cl | COSCH(CH$_3$)COOCH$_2$CH=CH$_2$ |

TABLE 4-continued

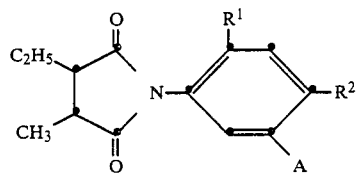

| No. | R¹ | R² | A |
|---|---|---|---|
| 4.24 | F | Cl | OH |
| 4.25 | F | Br | OH |
| 4.26 | F | Cl | OCH₃ |
| 4.27 | F | Cl | OCH(CH₃)₂ |
| 4.28 | F | Br | OCH₂CH=CH₂ |
| 4.29 | F | Cl | OCH₂CH=CHCl |
| 4.30 | F | Cl | OCH₂CCl=CH₂ |
| 4.31 | F | Cl | OCH₂COOCH₃ |
| 4.32 | F | Cl | OCH₂COOCH(CH₃)₂ |
| 4.33 | F | Cl | SH |
| 4.34 | F | Br | SH |
| 4.35 | F | Cl | SCH₃ |
| 4.36 | F | Cl | SCH(CH₃)₂ |
| 4.37 | F | Cl | SCH₂CH=CHCl |
| 4.38 | F | Cl | SCH₂COOH |
| 4.39 | F | Br | SCH₂COOH |
| 4.40 | F | Cl | SCH(CH₃)COOH |
| 4.41 | F | Cl | SCH₂COOCH₃ |
| 4.42 | F | Cl | SCH(CH₃)COOCH₃ |
| 4.43 | F | Cl | OCH₂C≡CH |
| 4.44 | F | Cl | OCH(CH₃)COOCH₃ |

TABLE 5

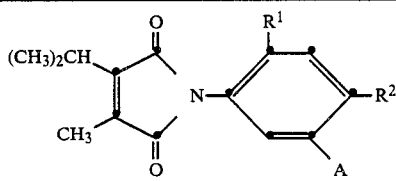

| No. | R¹ | R² | A |
|---|---|---|---|
| 5.01 | F | Cl | COCH₃ |
| 5.02 | F | Cl | COCH₂Cl |
| 5.03 | F | Cl | COCF₃ |
| 5.04 | F | | COCH₃ |
| 5.05 | F | Cl | C(CH₃)=N—OH |
| 5.06 | F | Cl | C(CH₃)=N—OCH₃ |
| 5.07 | F | Cl | C(CN)=N—OH |
| 5.08 | F | Br | C(CN)=N—OC₂H₅ |
| 5.09 | F | Cl | C(CN)=NOCH(CH₃)COOCH₃ |
| 5.10 | F | Cl | ![dioxolane with CH₃] |
| 5.11 | F | Cl | ![dioxolane with CH₃, CH₃] |
| 5.12 | F | Cl | ![dioxolane with CH₂Cl, CH₃] |
| 5.13 | F | Cl | COOH |

TABLE 5-continued

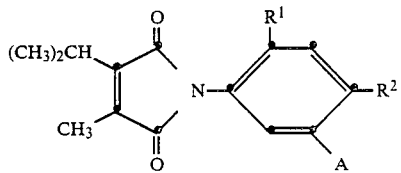

| No. | R¹ | R² | A |
|---|---|---|---|
| 5.14 | F | Br | COOH |
| 5.15 | F | Cl | COOCH₃ |
| 5.16 | F | Cl | COOCH(CH₃)₂ |
| 5.17 | H | Cl | COOH |
| 5.18 | H | Cl | COOCH₃ |
| 5.19 | H | Cl | COOCH(CH₃)₂ |
| 5.20 | F | Cl | COSCH₂COOCH₃ |
| 5.21 | F | Cl | COSCH₂COOCH₂(CH₃)₂ |
| 5.22 | F | Cl | COSCH(CH₃)COOCH₃ |
| 5.23 | F | Cl | COSCH(CH₃)COOCH₂CH=CH₂ |
| 5.24 | F | Cl | OH |
| 5.25 | F | Br | OH |
| 5.26 | F | Cl | OCH₃ |
| 5.27 | F | Cl | OCH(CH₃)₂ n$_D^{23}$ = 1,5298 |
| 5.28 | F | Br | OCH₂CH=CH₂ |
| 5.29 | F | Cl | OCH₂CH=CHCl |
| 5.30 | F | Cl | OCH₂CCl=CH₂ |
| 5.31 | F | Cl | OCH₂COOCH₃ |
| 5.32 | F | Cl | OCH₂COOCH(CH₃)₂ |
| 5.33 | F | Cl | SH |
| 5.34 | F | Br | SH |
| 5.35 | F | Cl | SCH₃ |
| 5.36 | F | Cl | SCH(CH₃)₂ |
| 5.37 | F | Cl | SCH₂CH=CHCl |
| 5.38 | F | Cl | SCH₂COOH |
| 5.39 | F | Br | SCH₂COOH |
| 5.40 | F | Cl | SCH(CH₃)COOH |
| 5.41 | F | Cl | SCH₂COOCH₃ |
| 5.42 | F | Cl | SCH(CH₃)COOCH₃ |
| 5.43 | F | Cl | OCH₂C≡CH |
| 5.44 | F | Cl | OCH(CH₃)COOCH₃ |

TABLE 6

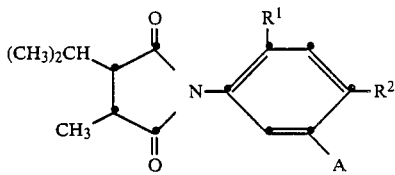

| No. | R¹ | R² | A |
|---|---|---|---|
| 6.01 | F | Cl | COCH₃ |
| 6.02 | F | Cl | COCH₂Cl |
| 6.03 | F | Cl | COCF₃ |
| 6.04 | F | | COCH₃ |
| 6.05 | F | Cl | C(CH₃)=N—OH |
| 6.06 | F | Cl | C(CH₃)=N—OCH₃ |
| 6.07 | F | Cl | C(CN)=N—OH |
| 6.08 | F | Br | C(CN)=N—OC₂H₅ |
| 6.09 | F | Cl | C(CN)=NOCH(CH₃)COOCH₃ |
| 6.10 | F | Cl | ![dioxolane with CH₃] |
| 6.11 | F | Cl | ![dioxolane with CH₃, CH₃] |

TABLE 6-continued

Structure: (CH₃)₂CH and CH₃ substituted diketone-N-aryl with R¹, R², A substituents

| No. | R¹ | R² | A |
|---|---|---|---|
| 6.12 | F | Cl | cyclic C(CH₃)(O-CH₂Cl-O) |
| 6.13 | F | Cl | COOH |
| 6.14 | F | Br | COOH |
| 6.15 | F | Cl | COOCH₃ |
| 6.16 | F | Cl | COOCH(CH₃)₂ |
| 6.17 | H | Cl | COOH |
| 6.18 | H | Cl | COOCH₃ |
| 6.19 | H | Cl | COOCH(CH₃)₂ |
| 6.20 | F | Cl | COSCH₂COOCH₃ |
| 6.21 | F | Cl | COSCH₂COOCH₂(CH₃)₂ |
| 6.22 | F | Cl | COSCH₂(CH₃)COOCH₃ |
| 6.23 | F | Cl | COSCH(CH₃)COOCH₂CH=CH₂ |
| 6.24 | F | Cl | OH |
| 6.25 | F | Br | OH |
| 6.26 | F | Cl | OCH₃ |
| 6.27 | F | Cl | OCH(CH₃)₂ m.p. 71–73° |
| 6.28 | F | Br | OCH₂CH=CH₂ |
| 6.29 | F | Cl | OCH₂CH=CHCl |
| 6.30 | F | Cl | OCH₂CCl=CH₂ |
| 6.31 | F | Cl | OCH₂COOCH₃ |
| 6.32 | F | Cl | OCH₂COOCH(CH₃)₂ |
| 6.33 | F | Cl | SH |
| 6.34 | F | Br | SH |
| 6.35 | F | Cl | SCH₃ |
| 6.36 | F | Cl | SCH(CH₃)₂ |
| 6.37 | F | Cl | SCH₂CH=CHCl |
| 6.38 | F | Cl | SCH₂COOH |
| 6.39 | F | Br | SCH₂COOH |
| 6.40 | F | Cl | SCH(CH₃)COOH |
| 6.41 | F | Cl | SCH₂COOCH₃ |
| 6.42 | F | Cl | SCH(CH₃)COOCH₃ |
| 6.43 | F | Cl | OCH₂C≡CH |
| 6.44 | F | Cl | OCH(CH₃)COOCH₃ |

TABLE 7

Structure: (CH₃)₂CH substituted maleimide-N-aryl with R¹, R², A substituents

| No. | R¹ | R² | A |
|---|---|---|---|
| 7.01 | F | Cl | COCH₃ |
| 7.02 | F | Cl | COCH₂Cl |
| 7.03 | F | Cl | COCF₃ |
| 7.04 | F |  | COCH₃ |
| 7.05 | F | Cl | C(CH₃)=N—OH |
| 7.06 | F | Cl | C(CH₃)=N—OCH₃ |
| 7.07 | F | Cl | C(CN)=N—OH |
| 7.08 | F | Br | C(CN)=N—OC₂H₅ |
| 7.09 | F | Cl | C(CN)=NOCH(CH₃)COOCH₃ |
| 7.10 | F | Cl | cyclic C(CH₃)(O-CH₂-O) |
| 7.11 | F | Cl | cyclic C(CH₃)(O-CH₃-O) |
| 7.12 | F | Cl | cyclic C(CH₃)(O-CH₂Cl-O) |
| 7.13 | F | Cl | COOH |
| 7.14 | F | Br | COOH |
| 7.15 | F | Cl | COOCH₃ |
| 7.16 | F | Cl | COOCH(CH₃)₂ |
| 7.17 | H | Cl | COOH |
| 7.18 | H | Cl | COOCH₃ |
| 7.19 | H | Cl | COOCH(CH₃)₂ |
| 7.20 | F | Cl | COSCH₂COOCH₃ |
| 7.21 | F | Cl | COSCH₂COOCH₂(CH₃)₂ |
| 7.22 | F | Cl | COSCH₂(CH₃)COOCH₃ |
| 7.23 | F | Cl | COSCH(CH₃)COOCH₂CH=CH₂ |
| 7.24 | F | Cl | OH |
| 7.25 | F | Br | OH |
| 7.26 | F | Cl | OCH₃ |
| 7.27 | F | Cl | OCH(CH₃)₂ |
| 7.28 | F | Br | OCH₂CH=CH₂ |
| 7.29 | F | Cl | OCH₂CH=CHCl |
| 7.30 | F | Cl | OCH₂CCl=CH₂ |
| 7.31 | F | Cl | OCH₂COOCH₃ |
| 7.32 | F | Cl | OCH₂COOCH(CH₃)₂ |
| 7.33 | F | Cl | SH |
| 7.34 | F | Br | SH |
| 7.35 | F | Cl | SCH₃ |
| 7.36 | F | Cl | SCH(CH₃)₂ |
| 7.37 | F | Cl | SCH₂CH=CHCl |
| 7.38 | F | Cl | SCH₂COOH |
| 7.39 | F | Br | SCH₂COOH |
| 7.40 | F | Cl | SCH(CH₃)COOH |
| 7.41 | F | Cl | SCH₂COOCH₃ |
| 7.42 | F | Cl | SCH(CH₃)COOCH₃ |
| 7.43 | F | Cl | OCH₂C≡CH |
| 7.44 | F | Cl | OCH(CH₃)COOCH₃ |

TABLE 8

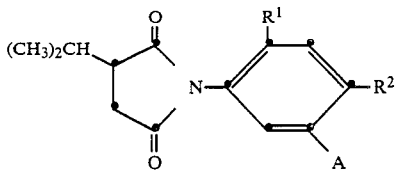

| No. | R¹ | R² | A |
|---|---|---|---|
| 8.01 | F | Cl | COCH₃ |
| 8.02 | F | Cl | COCH₂Cl |
| 8.03 | F | Cl | COCF₃ |
| 8.04 | F | | COCH₃ |
| 8.05 | F | Cl | C(CH₃)=N—OH |
| 8.06 | F | Cl | C(CH₃)=N—OCH₃ |
| 8.07 | F | Cl | C(CN)=N—OH |
| 8.08 | F | Br | C(CN)=N—OC₂H₅ |
| 8.09 | F | Cl | C(CN)=NOCH(CH₃)COOCH₃ |
| 8.10 | F | Cl | (dioxolane with CH₃) |
| 8.11 | F | Cl | (dioxolane with CH₃, CH₃) |
| 8.12 | F | Cl | (dioxolane with CH₂Cl, CH₃) |
| 8.13 | F | Cl | COOH |
| 8.14 | F | Br | COOH |
| 8.15 | F | Cl | COOCH₃ |
| 8.16 | F | Cl | COOCH(CH₃)₂ |
| 8.17 | H | Cl | COOH |
| 8.18 | H | Cl | COOCH₃ |
| 8.19 | H | Cl | COOCH(CH₃)₂ |
| 8.20 | F | Cl | COSCH₂COOCH₃ |
| 8.21 | F | Cl | COSCH₂COOCH₂(CH₃)₂ |
| 8.22 | F | Cl | COSCH₂(CH₃)COOCH₃ |
| 8.23 | F | Cl | COSCH(CH₃)COOCH₂CH=CH₂ |
| 8.24 | F | Cl | OH |
| 8.25 | F | Br | OH |
| 8.26 | F | Cl | OCH₃ |
| 8.27 | F | Cl | OCH(CH₃)₂  m.p. 119-120° |
| 8.28 | F | Br | OCH₂CH=CH₂ |
| 8.29 | F | Cl | OCH₂CH=CHCl |
| 8.30 | F | Cl | OCH₂CCl=CH₂ |
| 8.31 | F | Cl | OCH₂COOCH₃ |
| 8.32 | F | Cl | OCH₂COOCH(CH₃)₂ |
| 8.33 | F | Cl | SH |
| 8.34 | F | Br | SH |
| 8.35 | F | Cl | SCH₃ |
| 8.36 | F | Cl | SCH(CH₃)₂ |
| 8.37 | F | Cl | SCH₂CH=CHCl |
| 8.38 | F | Cl | SCH₂COOH |
| 8.39 | F | Br | SCH₂COOH |
| 8.40 | F | Cl | SCH(CH₃)COOH |
| 8.41 | F | Cl | SCH₂COOCH₃ |
| 8.42 | F | Cl | SCH(CH₃)COOCH₃ |
| 8.43 | F | Cl | OCH₂C≡CH |
| 8.44 | F | Cl | OCH(CH₃)COOCH₃ |

TABLE 9

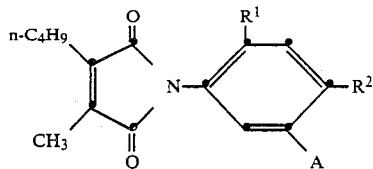

| No. | R¹ | R² | A | |
|---|---|---|---|---|
| 9.01 | F | Cl | COCH₃ | |
| 9.02 | F | Cl | COCH₂Cl | |
| 9.03 | F | Cl | COCF₃ | |
| 9.04 | F | | COCH₃ | |
| 9.05 | F | Cl | C(CH₃)=N—OH | |
| 9.06 | F | Cl | C(CH₃)=N—OCH₃ | |
| 9.07 | F | Cl | C(CN)=N—OH | |
| 9.08 | F | Br | C(CN)=N—OC₂H₅ | |
| 9.09 | F | Cl | C(CN)=NOCH(CH₃)COOCH₃ | |
| 9.10 | F | Cl | (dioxolane with CH₃) | |
| 9.11 | F | Cl | (dioxolane with CH₃, CH₃) | |
| 9.12 | F | Cl | (dioxolane with CH₂Cl, CH₃) | |
| 9.13 | F | Cl | COOH | |
| 9.14 | F | Br | COOH | |
| 9.15 | F | Cl | COOCH₃ | |
| 9.16 | F | Cl | COOCH(CH₃)₂ | |
| 9.17 | H | Cl | COOH | |
| 9.18 | H | Cl | COOCH₃ | |
| 9.19 | H | Cl | COOCH(CH₃)₂ | |
| 9.20 | F | Cl | COSCH₂COOCH₃ | |
| 9.21 | F | Cl | COSCH₂COOCH₂(CH₃)₂ | |
| 9.22 | F | Cl | COSCH₂(CH₃)COOCH₃ | |
| 9.23 | F | Cl | COSCH(CH₃)COOCH₂CH=CH₂ | |
| 9.24 | F | Cl | OH | |
| 9.25 | F | Br | OH | |
| 9.26 | F | Cl | OCH₃ | |
| 9.27 | F | Cl | OCH(CH₃)₂ | oil |
| 9.28 | F | Br | OCH₂CH=CH₂ | |
| 9.29 | F | Cl | OCH₂CH=CHCl | |
| 9.30 | F | Cl | OCH₂CCl=CH₂ | |
| 9.31 | F | Cl | OCH₂COOCH₃ | |
| 9.32 | F | Cl | OCH₂COOCH(CH₃)₂ | |
| 9.33 | F | Cl | SH | |
| 9.34 | F | Br | SH | |
| 9.35 | F | Cl | SCH₃ | |
| 9.36 | F | Cl | SCH(CH₃)₂ | |
| 9.37 | F | Cl | SCH₂CH=CHCl | |
| 9.38 | F | Cl | SCH₂COOH | |
| 9.39 | F | Br | SCH₂COOH | |
| 9.40 | F | Cl | SCH(CH₃)COOH | |
| 9.41 | F | Cl | SCH₂COOCH₃ | |
| 9.42 | F | Cl | SCH(CH₃)COOCH₃ | |
| 9.43 | F | Cl | OCH₂C≡CH | |
| 9.44 | F | Cl | OCH(CH₃)COOCH₃ | |

TABLE 10

[Structure: n-C4H9 and CH3 substituents on a dione connected via N to a phenyl ring with R¹, R², and A substituents]

| No. | R¹ | R² | A |
|---|---|---|---|
| 10.01 | F | Cl | COCH₃ |
| 10.02 | F | Cl | COCH₂Cl |
| 10.03 | F | Cl | COCF₃ |
| 10.04 | F | | COCH₃ |
| 10.05 | F | Cl | C(CH₃)=N—OH |
| 10.06 | F | Cl | C(CH₃)=N—OCH₃ |
| 10.07 | F | Cl | C(CN)=N—OH |
| 10.08 | F | Br | C(CN)=N—OC₂H₅ |
| 10.09 | F | Cl | C(CN)=NOCH(CH₃)COOCH₃ |
| 10.10 | F | Cl | [cyclic: C(CH₃) with two O linked to a carbon] |
| 10.11 | F | Cl | [cyclic: C(CH₃) with two O linked to C(CH₃)] |
| 10.12 | F | Cl | [cyclic: C(CH₃) with two O linked to C(CH₂Cl)] |
| 10.13 | F | Cl | COOH |
| 10.14 | F | Br | COOH |
| 10.15 | F | Cl | COOCH₃ |
| 10.16 | F | Cl | COOCH(CH₃)₂ |
| 10.17 | H | Cl | COOH |
| 10.18 | H | Cl | COOCH₃ |
| 10.19 | H | Cl | COOCH(CH₃)₂ |
| 10.20 | F | Cl | COSCH₂COOCH₃ |
| 10.21 | F | Cl | COSCH₂COOCH₂(CH₃)₂ |
| 10.22 | F | Cl | COSCH(CH₃)COOCH₃ |
| 10.23 | F | Cl | COSCH(CH₃)COOCH₂CH=CH₂ |
| 10.24 | F | Cl | OH |
| 10.25 | F | Br | OH |
| 10.26 | F | Cl | OCH₃ |
| 10.27 | F | Cl | OCH(CH₃)₂ |
| 10.28 | F | Br | OCH₂CH=CH₂ |
| 10.29 | F | Cl | OCH₂CH=CHCl |
| 10.30 | F | Cl | OCH₂CCl=CH₂ |
| 10.31 | F | Cl | OCH₂COOCH₃ |
| 10.32 | F | Cl | OCH₂COOCH(CH₃)₂ |
| 10.33 | F | Cl | SH |
| 10.34 | F | Br | SH |
| 10.35 | F | Cl | SCH₃ |
| 10.36 | F | Cl | SCH(CH₃)₂ |
| 10.37 | F | Cl | SCH₂CH=CHCl |
| 10.38 | F | Cl | SCH₂COOH |
| 10.39 | F | Br | SCH₂COOH |
| 10.40 | F | Cl | SCH(CH₃)COOH |
| 10.41 | F | Cl | SCH₂COOCH₃ |
| 10.42 | F | Cl | SCH(CH₃)COOCH₃ |
| 10.43 | F | Cl | OCH₂C≡CH |
| 10.44 | F | Cl | OCH(CH₃)COOCH₃ |

TABLE 11

[Structure: CH3 substituent on a dione (with double bond) connected via N to a phenyl ring with R¹, R², and A substituents]

| No. | R¹ | R² | A | |
|---|---|---|---|---|
| 11.01 | F | Cl | COCH₃ | |
| 11.02 | F | Cl | COCH₂Cl | |
| 11.03 | F | Cl | COCF₃ | |
| 11.04 | F | | COCH₃ | |
| 11.05 | F | Cl | C(CH₃)=N—OH | |
| 11.06 | F | Cl | C(CH₃)=N—OCH₃ | |
| 11.07 | F | Cl | C(CN)=N—OH | |
| 11.08 | F | Br | C(CN)=N—OC₂H₅ | |
| 11.09 | F | Cl | C(CN)=NOCH(CH₃)COOCH₃ | |
| 11.10 | F | Cl | [cyclic dioxolane with CH₃] | |
| 11.11 | F | Cl | [cyclic dioxolane with CH₃, CH₃] | |
| 11.12 | F | Cl | [cyclic dioxolane with CH₃, CH₂Cl] | |
| 11.13 | F | Cl | COOH | |
| 11.14 | F | Br | COOH | |
| 11.15 | F | Cl | COOCH₃ | |
| 11.16 | F | Cl | COOCH(CH₃)₂ | |
| 11.17 | H | Cl | COOH | |
| 11.18 | H | Cl | COOCH₃ | |
| 11.19 | H | Cl | COOCH(CH₃)₂ | |
| 11.20 | F | Cl | COSCH₂COOCH₃ | |
| 11.21 | F | Cl | COSCH₂COOCH₂(CH₃)₂ | |
| 11.22 | F | Cl | COSCH(CH₃)COOCH₃ | |
| 11.23 | F | Cl | COSCH(CH₃)COOCH₂CH=CH₂ | |
| 11.24 | F | Cl | OH | |
| 11.25 | F | Br | OH | |
| 11.26 | F | Cl | OCH₃ | |
| 11.27 | F | Cl | OCH(CH₃)₂ | m.p. 68–70° |
| 11.28 | F | Br | OCH₂CH=CH₂ | |
| 11.29 | F | Cl | OCH₂CH=CHCl | |
| 11.30 | F | Cl | OCH₂CCl=CH₂ | |
| 11.31 | F | Cl | OCH₂COOCH₃ | |
| 11.32 | F | Cl | OCH₂COOCH(CH₃)₂ | |
| 11.33 | F | Cl | SH | |
| 11.34 | F | Br | SH | |
| 11.35 | F | Cl | SCH₃ | |
| 11.36 | F | Cl | SCH(CH₃)₂ | |
| 11.37 | F | Cl | SCH₂CH=CHCl | |
| 11.38 | F | Cl | SCH₂COOH | |
| 11.39 | F | Br | SCH₂COOH | |
| 11.40 | F | Cl | SCH(CH₃)COOH | |
| 11.41 | F | Cl | SCH₂COOCH₃ | |
| 11.42 | F | Cl | SCH(CH₃)COOCH₃ | |
| 11.43 | F | Cl | OCH₂C≡CH | |
| 11.44 | F | Cl | OCH(CH₃)COOCH₃ | |

TABLE 12

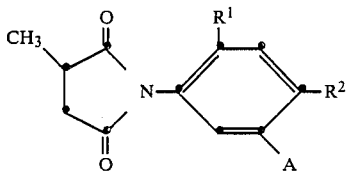

| No. | R¹ | R² | A |
|---|---|---|---|
| 12.01 | F | Cl | COCH₃ |
| 12.02 | F | Cl | COCH₂Cl |
| 12.03 | F | Cl | COCF₃ |
| 12.04 | F | | COCH₃ |
| 12.05 | F | Cl | C(CH₃)=N—OH |
| 12.06 | F | Cl | C(CH₃)=N—OCH₃ |
| 12.07 | F | Cl | C(CN)=N—OH |
| 12.08 | F | Br | C(CN)=N—OC₂H₅ |
| 12.09 | F | Cl | C(CN)=NOCH(CH₃)COOCH₃ |
| 12.10 | F | Cl | (cyclic OC(CH₃)O—) |
| 12.11 | F | Cl | (cyclic OC(CH₃)(CH₃)O—) |
| 12.12 | F | Cl | (cyclic OC(CH₂Cl)(CH₃)O—) |
| 12.13 | F | Cl | COOH |
| 12.14 | F | Br | COOH |
| 12.15 | F | Cl | COOCH₃ |
| 12.16 | F | Cl | COOCH(CH₃)₂ |
| 12.17 | H | Cl | COOH |
| 12.18 | H | Cl | COOCH₃ |
| 12.19 | H | Cl | COOCH(CH₃)₂ |
| 12.20 | F | Cl | COSCH₂COOCH₃ |
| 12.21 | F | Cl | COSCH₂COOCH₂(CH₃)₂ |
| 12.22 | F | Cl | COSCH₂(CH₃)COOCH₃ |
| 12.23 | F | Cl | COSCH(CH₃)COOCH₂CH=CH₂ |
| 12.24 | F | Cl | OH |
| 12.25 | F | Br | OH |
| 12.26 | F | Cl | OCH₃ |
| 12.27 | F | Cl | OCH(CH₃)₂ |
| 12.28 | F | Br | OCH₂CH=CH₂ |
| 12.29 | F | Cl | OCH₂CH=CHCl |
| 12.30 | F | Cl | OCH₂CCl=CH₂ |
| 12.31 | F | Cl | OCH₂COOCH₃ |
| 12.32 | F | Cl | OCH₂COOCH(CH₃)₂ |
| 12.33 | F | Cl | SH |
| 12.34 | F | Br | SH |
| 12.35 | F | Cl | SCH₃ |
| 12.36 | F | Cl | SCH(CH₃)₂ |
| 12.37 | F | Cl | SCH₂CH=CHCl |
| 12.38 | F | Cl | SCH₂COOH |
| 12.39 | F | Br | SCH₂COOH |
| 12.40 | F | Cl | SCH(CH₃)COOH |
| 12.41 | F | Cl | SCH₂COOCH₃ |
| 12.42 | F | Cl | SCH(CH₃)COOCH₃ |
| 12.43 | F | Cl | OCH₂C≡CH |
| 12.44 | F | Cl | OCH(CH₃)COOCH₃ |

TABLE 13

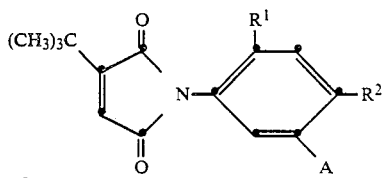

| No. | R¹ | R² | A | |
|---|---|---|---|---|
| 13.01 | F | Cl | COCH₃ | |
| 13.02 | F | Cl | COCH₂Cl | |
| 13.03 | F | Cl | COCF₃ | |
| 13.04 | F | | COCH₃ | |
| 13.05 | F | Cl | C(CH₃)=N—OH | |
| 13.06 | F | Cl | C(CH₃)=N—OCH₃ | |
| 13.07 | F | Cl | C(CN)=N—OH | |
| 13.08 | F | Br | C(CN)=N—OC₂H₅ | |
| 13.09 | F | Cl | C(CN)=NOCH(CH₃)COOCH₃ | |
| 13.10 | F | Cl | (cyclic OC(CH₃)O—) | |
| 13.11 | F | Cl | (cyclic OC(CH₃)(CH₃)O—) | |
| 13.12 | F | Cl | (cyclic OC(CH₂Cl)(CH₃)O—) | |
| 13.13 | F | Cl | COOH | |
| 13.14 | F | Br | COOH | |
| 13.15 | F | Cl | COOCH₃ | |
| 13.16 | F | Cl | COOCH(CH₃)₂ | |
| 13.17 | H | Cl | COOH | |
| 13.18 | H | Cl | COOCH₃ | |
| 13.19 | H | Cl | COOCH(CH₃)₂ | |
| 13.20 | F | Cl | COSCH₂COOCH₃ | |
| 13.21 | F | Cl | COSCH₂COOCH₂(CH₃)₂ | |
| 13.22 | F | Cl | COSCH₂(CH₃)COOCH₃ | |
| 13.23 | F | Cl | COSCH(CH₃)COOCH₂CH=CH₂ | |
| 13.24 | F | Cl | OH | |
| 13.25 | F | Br | OH | |
| 13.26 | F | Cl | OCH₃ | |
| 13.27 | F | Cl | OCH(CH₃)₂ | |
| 13.28 | F | Br | OCH₂CH=CH₂ | |
| 13.29 | F | Cl | OCH₂CH=CHCl | |
| 13.30 | F | Cl | OCH₂CCl=CH₂ | |
| 13.31 | F | Cl | OCH₂COOCH₃ | |
| 13.32 | F | Cl | OCH₂COOCH(CH₃)₂ | |
| 13.33 | F | Cl | SH | |
| 13.34 | F | Br | SH | |
| 13.35 | F | Cl | SCH₃ | |
| 13.36 | F | Cl | SCH(CH₃)₂ | |
| 13.37 | F | Cl | SCH₂CH=CHCl | |
| 13.38 | F | Cl | SCH₂COOH | |
| 13.39 | F | Br | SCH₂COOH | |
| 13.40 | F | Cl | SCH(CH₃)COOH | |
| 13.41 | F | Cl | SCH₂COOCH₃ | |
| 13.42 | F | Cl | SCH(CH₃)COOCH₃ | |
| 13.43 | H | Cl | H | m.p. 101–102° |
| 13.44 | H | Br | H | |
| 13.45 | F | Cl | OC₂H₅ | |
| 13.46 | F | Cl | OC₃H₇—n | |
| 13.47 | F | Cl | OC₄H₉—n | |
| 13.48 | F | Cl | OCH(CH₃)C₂H₅ | |
| 13.49 | F | Cl | OCH₂CH(CH₃)₂ | |
| 13.50 | F | Cl | OCH₂C≡CH | $n_D^{22} = 1,5363$ |

TABLE 13-continued

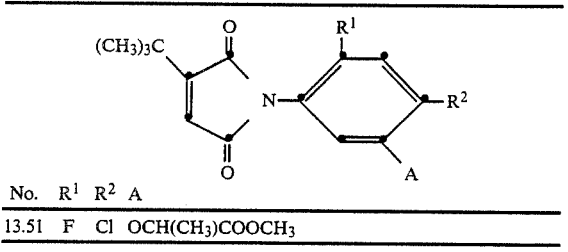

| No. | R¹ | R² | A |
|---|---|---|---|
| 13.51 | F | Cl | OCH(CH₃)COOCH₃ |

TABLE 14

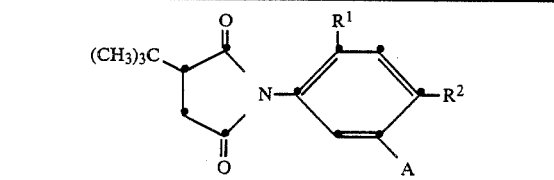

| No. | R¹ | R² | A |
|---|---|---|---|
| 14.01 | F | Cl | COCH₃ |
| 14.02 | F | Cl | COCH₂Cl |
| 14.03 | F | Cl | COCF₃ |
| 14.04 | F |  | COCH₃ |
| 14.05 | F | Cl | C(CH₃)=N—OH |
| 14.06 | F | Cl | C(CH₃)=N—OCH₃ |
| 14.07 | F | Cl | C(CN)=N—OH |
| 14.08 | F | Br | C(CN)=N—OC₂H₅ |
| 14.09 | F | Cl | C(CN)=NOCH(CH₃)COOCH₃ |
| 14.10 | F | Cl | 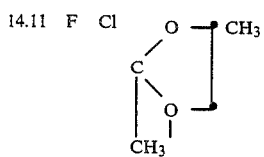 |
| 14.11 | F | Cl |  |
| 14.12 | F | Cl | 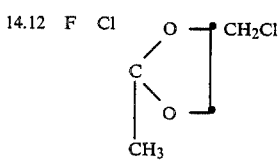 |
| 14.13 | F | Cl | COOH |
| 14.14 | F | Br | COOH |
| 14.15 | F | Cl | COOCH₃ |
| 14.16 | F | Cl | COOCH(CH₃)₂ |
| 14.17 | H | Cl | COOH |
| 14.18 | H | Cl | COOCH₃ |
| 14.19 | H | Cl | COOCH(CH₃)₂ |
| 14.20 | F | Cl | COSCH₂COOCH₃ |
| 14.21 | F | Cl | COSCH₂COOCH₂(CH₃)₂ |
| 14.22 | F | Cl | COSCH₂(CH₃)COOCH₃ |
| 14.23 | F | Cl | COSCH(CH₃)COOCH₂CH=CH₂ |
| 14.24 | F | Cl | OH |
| 14.25 | F | Br | OH |
| 14.26 | F | Cl | OCH₃ |
| 14.27 | F | Cl | OCH(CH₃)₂    $n_D^{22} = 1.5185$ |
| 14.28 | F | Br | OCH₂CH=CH₂ |
| 14.29 | F | Cl | OCH₂CH=CHCl |
| 14.30 | F | Cl | OCH₂CCl=CH₂ |
| 14.31 | F | Cl | OCH₂COOCH₃ |
| 14.32 | F | Cl | OCH₂COOCH(CH₃)₂ |
| 14.33 | F | Cl | SH |
| 14.34 | F | Br | SH |

TABLE 14-continued

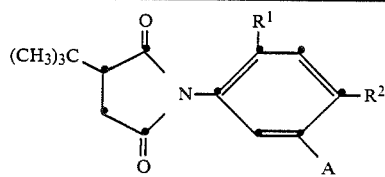

| No. | R¹ | R² | A |  |
|---|---|---|---|---|
| 14.35 | F | Cl | SCH₃ |  |
| 14.36 | F | Cl | SCH(CH₃)₂ |  |
| 14.37 | F | Cl | SCH₂CH=CHCl |  |
| 14.38 | F | Cl | SCH₂COOH |  |
| 14.39 | F | Br | SCH₂COOH |  |
| 14.40 | F | Cl | SCH(CH₃)COOH |  |
| 14.41 | F | Cl | SCH₂COOCH₃ |  |
| 14.42 | F | Cl | SCH(CH₃)COOCH₃ |  |
| 14.43 | H | Cl | H | m.p. 195–196° |
| 14.44 | F | Cl | OCH₂C≡CH |  |
| 14.45 | F | Cl | OCH(CH₃)COOCH₃ |  |

TABLE 15

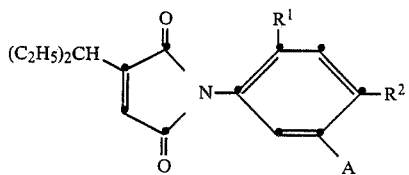

| No. | R¹ | R² | A |
|---|---|---|---|
| 15.01 | F | Cl | COCH₃ |
| 15.02 | F | Cl | COCH₂Cl |
| 15.03 | F | Cl | COCF₃ |
| 15.04 | F |  | COCH₃ |
| 15.05 | F | Cl | C(CH₃)=N—OH |
| 15.06 | F | Cl | C(CH₃)=N—OCH₃ |
| 15.07 | F | Cl | C(CN)=N—OH |
| 15.08 | F | Br | C(CN)=N—OC₂H₅ |
| 15.09 | F | Cl | C(CN)=NOCH(CH₃)COOCH₃ |
| 15.10 | F | Cl |  |
| 15.11 | F | Cl |  |
| 15.12 | F | Cl | 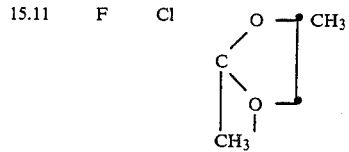 |
| 15.13 | F | Cl | COOH |
| 15.14 | F | Br | COOH |
| 15.15 | F | Cl | COOCH₃ |
| 15.16 | F | Cl | COOCH(CH₃)₂ |
| 15.17 | H | Cl | COOH |
| 15.18 | H | Cl | COOCH₃ |
| 15.19 | H | Cl | COOCH(CH₃)₂ |
| 15.20 | F | Cl | COSCH₂COOCH₃ |
| 15.21 | F | Cl | COSCH₂COOCH₂(CH₃)₂ |
| 15.22 | F | Cl | COSCH₂(CH₃)COOCH₃ |
| 15.23 | F | Cl | COSCH(CH₃)COOCH₂CH=CH₂ |

TABLE 15-continued

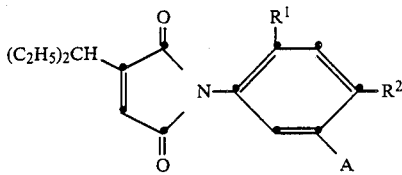

| No. | R¹ | R² | A |
|---|---|---|---|
| 15.24 | F | Cl | OH |
| 15.25 | F | Br | OH |
| 15.26 | F | Cl | OCH₃ |
| 15.27 | F | Cl | OCH(CH₃)₂ |
| 15.28 | F | Br | OCH₂CH=CH₂ |
| 15.29 | F | Cl | OCH₂CH=CHCl |
| 15.30 | F | Cl | OCH₂CCl=CH₂ |
| 15.31 | F | Cl | OCH₂COOCH₃ |
| 15.32 | F | Cl | OCH₂COOCH(CH₃)₂ |
| 15.33 | F | Cl | SH |
| 15.34 | F | Br | SH |
| 15.35 | F | Cl | SCH₃ |
| 15.36 | F | Cl | SCH(CH₃)₂ |
| 15.37 | F | Cl | SCH₂CH=CHCl |
| 15.38 | F | Cl | SCH₂COOH |
| 15.39 | F | Br | SCH₂COOH |
| 15.40 | F | Cl | SCH(CH₃)COOH |
| 15.41 | F | Cl | SCH₂COOCH₃ |
| 15.42 | F | Cl | SCH(CH₃)COOCH₃ |
| 15.43 | F | Cl | OCH₂C≡CH |
| 15.44 | F | Cl | OCH(CH₃)COOCH₃ |

TABLE 16

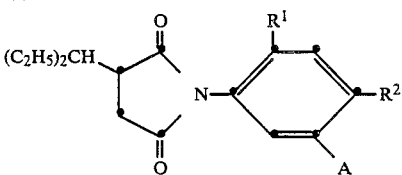

| No. | R¹ | R² | A |
|---|---|---|---|
| 16.01 | F | Cl | COCH₃ |
| 16.02 | F | Cl | COCH₂Cl |
| 16.03 | F | Cl | COCF₃ |
| 16.04 | F | | COCH₃ |
| 16.05 | F | Cl | C(CH₃)=N—OH |
| 16.06 | F | Cl | C(CH₃)=N—OCH₃ |
| 16.07 | F | Cl | C(CN)=N—OH |
| 16.08 | F | Br | C(CN)=N—OC₂H₅ |
| 16.09 | F | Cl | C(CN)=NOCH(CH₃)COOCH₃ |
| 16.10 | F | Cl | 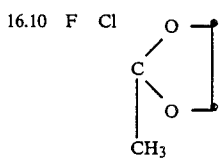 |
| 16.11 | F | Cl | 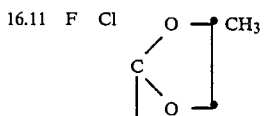 |
| 16.12 | F | Cl | 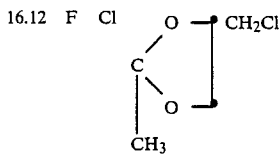 |
| 16.13 | F | Cl | COOH |

TABLE 16-continued

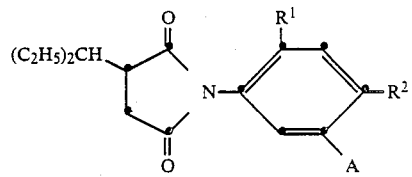

| No. | R¹ | R² | A | |
|---|---|---|---|---|
| 16.14 | F | Br | COOH | |
| 16.15 | F | Cl | COOCH₃ | |
| 16.16 | F | Cl | COOCH(CH₃)₂ | |
| 16.17 | H | Cl | COOH | |
| 16.18 | H | Cl | COOCH₃ | |
| 16.19 | H | Cl | COOCH(CH₃)₂ | |
| 16.20 | F | Cl | COSCH₂COOCH₃ | |
| 16.21 | F | Cl | COSCH₂COOCH₂(CH₃)₂ | |
| 16.22 | F | Cl | COSCH₂(CH₃)COOCH₃ | |
| 16.23 | F | Cl | COSCH(CH₃)COOCH₂CH=CH₂ | |
| 16.24 | F | Cl | OH | |
| 16.25 | F | Br | OH | |
| 16.26 | F | Cl | OCH₃ | |
| 16.27 | F | Cl | OCH(CH₃)₂ | $n_D^{22} = 1.5229$ |
| 16.28 | F | Br | OCH₂CH=CH₂ | |
| 16.29 | F | Cl | OCH₂CH=CHCl | |
| 16.30 | F | Cl | OCH₂CCl=CH₂ | |
| 16.31 | F | Cl | OCH₂COOCH₃ | |
| 16.32 | F | Cl | OCH₂COOCH(CH₃)₂ | |
| 16.33 | F | Cl | SH | |
| 16.34 | F | Br | SH | |
| 16.35 | F | Cl | SCH₃ | |
| 16.36 | F | Cl | SCH(CH₃)₂ | |
| 16.37 | F | Cl | SCH₂CH=CHCl | |
| 16.38 | F | Cl | SCH₂COOH | |
| 16.39 | F | Br | SCH₂COOH | |
| 16.40 | F | Cl | SCH(CH₃)COOH | |
| 16.41 | F | Cl | SCH₂COOCH₃ | |
| 16.42 | F | Cl | SCH(CH₃)COOCH₃ | |
| 16.43 | F | Cl | OCH₂C≡CH | |
| 16.44 | F | Cl | OCH(CH₃)COOCH₃ | |

TABLE 17

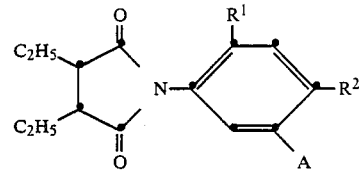

| No. | R¹ | R² | A |
|---|---|---|---|
| 17.01 | F | Cl | COCH₃ |
| 17.02 | F | Cl | COCH₂Cl |
| 17.03 | F | Cl | COCF₃ |
| 17.04 | F | | COCH₃ |
| 17.05 | F | Cl | C(CH₃)=N—OH |
| 17.06 | F | Cl | C(CH₃)=N—OCH₃ |
| 17.07 | F | Cl | C(CN)=N—OH |
| 17.08 | F | Br | C(CN)=N—OC₂H₅ |
| 17.09 | F | Cl | C(CN)=NOCH(CH₃)COOCH₃ |
| 17.10 | F | Cl | 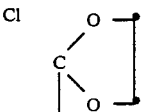 |
| 17.11 | F | Cl | 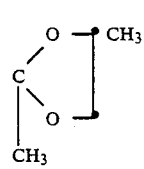 |

TABLE 17-continued

Structure: C₂H₅ and C₂H₅ substituents on a ring with two C=O groups, N connected to phenyl ring with R¹, R², A substituents.

| No. | R¹ | R² | A |
|---|---|---|---|
| 17.12 | F | Cl | (cyclic structure with O-CH₂Cl, C, O, CH₃) |
| 17.13 | F | Cl | COOH |
| 17.14 | F | Br | COOH |
| 17.15 | F | Cl | COOCH₃ |
| 17.16 | F | Cl | COOCH(CH₃)₂ |
| 17.17 | H | Cl | COOH |
| 17.18 | H | Cl | COOCH₃ |
| 17.19 | H | Cl | COOCH(CH₃)₂ |
| 17.20 | F | Cl | COSCH₂COOCH₃ |
| 17.21 | F | Cl | COSCH₂COOCH₂(CH₃) |
| 17.22 | F | Cl | COSCH₂(CH₃)COOCH₃ |
| 17.23 | F | Cl | COSCH(CH₃)COOCH₂CH=CH₂ |
| 17.24 | F | Cl | OH |
| 17.25 | F | Br | OH |
| 17.26 | F | Cl | OCH₃ |
| 17.27 | F | Cl | OCH(CH₃)₂ |
| 17.28 | F | Br | OCH₂CH=CH₂ |
| 17.29 | F | Cl | OCH₂CH=CHCl |
| 17.30 | F | Cl | OCH₂CCl=CH₂ |
| 17.31 | F | Cl | OCH₂COOCH₃ |
| 17.32 | F | Cl | OCH₂COOCH(CH₃)₂ |
| 17.33 | F | Cl | SH |
| 17.34 | F | Br | SH |
| 17.35 | F | Cl | SCH₃ |
| 17.36 | F | Cl | SCH(CH₃)₂ |
| 17.37 | F | Cl | SCH₂CH=CHCl |
| 17.38 | F | Cl | SCH₂COOH |
| 17.39 | F | Br | SCH₂COOH |
| 17.40 | F | Cl | SCH(CH₃)COOH |
| 17.41 | F | Cl | SCH₂COOCH₃ |
| 17.42 | F | Cl | SCH(CH₃)COOCH₃ |
| 17.43 | F | Cl | H | oil |
| 17.44 | F | Cl | OCH₂C≡CH |
| 17.45 | F | Cl | OCH(CH₃)COOCH₃ |

TABLE 18

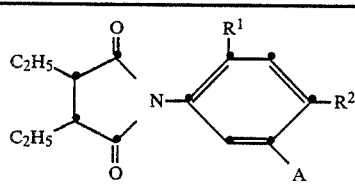

| No. | R¹ | R² | A |
|---|---|---|---|
| 18.01 | F | Cl | COCH₃ |
| 18.02 | F | Cl | COCH₂Cl |
| 18.03 | F | Cl | COCF₃ |
| 18.04 | F | | COCH₃ |
| 18.05 | F | Cl | C(CH₃)=N—OH |
| 18.06 | F | Cl | C(CH₃)=N—OCH₃ |
| 18.07 | F | Cl | C(CN)=N—OH |
| 18.08 | F | Br | C(CN)=N—OC₂H₅ |
| 18.09 | F | Cl | C(CN)=NOCH(CH₃)COOCH₃ |
| 18.10 | F | Cl | (cyclic O-C-O with CH₃) |
| 18.11 | F | Cl | (cyclic O-CH₃, C, O, CH₃) |
| 18.12 | F | Cl | (cyclic O-CH₂Cl, C, O, CH₃) |
| 18.13 | F | Cl | COOH |
| 18.14 | F | Br | COOH |
| 18.15 | F | Cl | COOCH₃ |
| 18.16 | F | Cl | COOCH(CH₃)₂ |
| 18.17 | H | Cl | COOH |
| 18.18 | H | Cl | COOCH₃ |
| 18.19 | H | Cl | COOCH(CH₃)₂ |
| 18.20 | F | Cl | COSCH₂COOCH₃ |
| 18.21 | F | Cl | COSCH₂COOCH₂(CH₃) |
| 18.22 | F | Cl | COSCH₂(CH₃)COOCH₃ |
| 18.23 | F | Cl | COSCH(CH₃)COOCH₂CH=CH₂ |
| 18.24 | F | Cl | OH |
| 18.25 | F | Br | OH |
| 18.26 | F | Cl | OCH₃ |
| 18.27 | F | Cl | OCH(CH₃)₂ | m.p. 80–81° |
| 18.28 | F | Br | OCH₂CH=CH₂ |
| 18.29 | F | Cl | OCH₂CH=CHCl |
| 18.30 | F | Cl | OCH₂CCl=CH₂ |
| 18.31 | F | Cl | OCH₂COOCH₃ |
| 18.32 | F | Cl | OCH₂COOCH(CH₃)₂ |
| 18.33 | F | Cl | SH |
| 18.34 | F | Br | SH |
| 18.35 | F | Cl | SCH₃ |
| 18.36 | F | Cl | SCH(CH₃)₂ |
| 18.37 | F | Cl | SCH₂CH=CHCl |
| 18.38 | F | Cl | SCH₂COOH |
| 18.39 | F | Br | SCH₂COOH |
| 18.40 | F | Cl | SCH(CH₃)COOH |
| 18.41 | F | Cl | SCH₂COOCH₃ |
| 18.42 | F | Cl | SCH(CH₃)COOCH₃ |
| 18.43 | F | Cl | H | m.p. 89–93° |
| 18.44 | F | Cl | OCH₂C≡CH |
| 18.45 | F | Cl | OCH(CH₃)COOCH₃ |

FORMULATION EXAMPLES

EXAMPLE 15

Formulation Examples for liquid active ingredients of the formula I (%=percent by weight)

| (a) emulsifiable concentrates | (a) | (b) | (c) |
|---|---|---|---|
| active ingredient according to Tables 1–10 | 20% | 40% | 50% |

-continued

| (a) emulsifiable concentrates | (a) | (b) | (c) |
| --- | --- | --- | --- |
| calcium dodecylbenzene-sulphonate | 5% | 8% | 5.8% |
| castor oil polyethylene glycol ether (36 moles of ethylene oxide) | 5% | — | — |
| tributylphenoyl polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be prepared from these concentrates by dilution with water.

| (b) solutions | (a) | (b) | (c) | (d) |
| --- | --- | --- | --- | --- |
| active ingredient according to Tables 1-10 | 80% | 10% | 5% | 95% |
| ethylene glycol monomethyl ether | 20% | — | — | — |
| polyethylene glycol MW 400 | — | 70% | — | — |
| N—methyl-2-pyrrolidone | — | 20% | — | — |
| epoxidised coconut oil | — | — | 94% | — |

The solutions are suitable for use in the form of very fine droplets.

| (c) granulates | (a) | (b) |
| --- | --- | --- |
| active ingredient according to Tables 1-10 | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent is then evaporated off in vacuo.

| (d) dusts | (a) | (b) |
| --- | --- | --- |
| active ingredient according to Tables 1-10 | 2% | 5% |
| highly dispersed silicic acid | 1% | 5% |
| talcum | 97% | — |
| kaolin | — | 90% |

Dusts that are ready for use are obtained by intimately mixing the carriers with the active ingredient.

EXAMPLE 16

Formulation Examples for solid active ingredients of the formula I (%=percent by weight)

| (a) wettable powders | (a) | (b) |
| --- | --- | --- |
| active ingredient according to Tables 1-10 | 20% | 60% |
| sodium lignosulphonate | 5% | 5% |
| sodium lauryl sulphate | — | 6% |
| octylphenolpolyethylene glycol ether (7-8 moles of ethylene oxide) | — | 2% |
| highly dispersed silicic acid | 5% | 27% |
| kaolin | 67% | — |

The active ingredient is mixed well with the additives and ground well in a suitable mill. A wettable powder is obtained which can be diluted with water to form a suspension of any desired concentration.

| (b) emulsifiable concentrate | |
| --- | --- |
| active ingredient according to Tables 1-10 | 10% |
| octylphenolpolyethylene gycol ether (4-5 moles of ethylene oxide) | 3% |
| calcium dodecylbenzenesulphonate | 3% |
| castor oil polyglycol ether (36 moles of ethylene oxide) | 4% |
| cyclohexanone | 30% |
| xylene mixture | 50% |

Emulsions of any desired concentration can be prepared from this concentrate by dilution with water.

| (c) dusts | (a) | (b) |
| --- | --- | --- |
| active ingredient according to Tables 1-10 | 5% | 8% |
| talcum | 95% | — |
| kaolin | — | 92% |

Dusts which are ready for use are obtained by mixing the active ingredient with the carrier and grinding them in a suitable mill.

| (d) extruder granulate | |
| --- | --- |
| active ingredient according to Tables 1-10 | 10% |
| sodium lignosulphonate | 2% |
| carboxymethylcellulose | 1% |
| kaolin | 87% |

The active ingredient is mixed with the additives, ground and moistened with water. This mixture is extruded and subsequently dried in a stream of air.

| (e) coated granulate (encapsulated granulate?) | |
| --- | --- |
| active ingredient according to Tables 1-10 | 3% |
| polyethylene glycol (MW 200) | 3% |
| kaolin | 94% |

The finely ground active ingredient is uniformly applied in a mixer to the kaolin moistened with the polyethylene glycol. Dust-free coated granulates are obtained in this manner.

| (f) suspension concentrate | |
| --- | --- |
| active ingredient according to Tables 1-10 | 40% |
| ethylene glycol | 10% |
| nonylphenolpolyethylene glycol ether (15 moles of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. In this manner, a suspension concentrate is obtained from which suspensions of any desired concentration can be prepared by dilution with water.

BIOLOGICAL EXAMPLES

EXAMPLE 17

Pre-emergence herbicidal action

In a greenhouse, immediately after sowing the test plants in seed trays, the surface of the soil is treated with an aqueous dispersion of the active ingredients obtained from a 25% emulsifiable concentrate. Concentrations of 4 kg of active ingredient/hectare are used. The seed trays are kept in a greenhouse at 22°–25° C. and 50–70% relative humidity and the test is evaluated after 3 weeks and the condition of the plants is assessed in accordance with the following scale.
1 plant dead or not germinated
2–4 severe damage
5 medium damage, plant remains withered
6–8 slight damage
9 plant growing normally, as untreated control plants The results of this test are recorded in the following Table:

| compound application rate | 1.27 | | | | 1.43 | | | |
|---|---|---|---|---|---|---|---|---|
| plant | 1000 | 500 | 250 | 125 | 1000 | 500 | 250 | 125 |
| barley | 6 | 8 | 9 | 9 | 3 | 4 | 8 | 9 |
| wheat | 8 | 9 | 9 | 9 | 7 | 8 | 9 | 9 |
| maize | 7 | 7 | 9 | 9 | 5 | 8 | 9 | 9 |
| rice | 4 | 6 | 8 | 9 | 7 | 8 | 9 | 9 |
| Avena fatua | 3 | 6 | 8 | 9 | 1 | 2 | 3 | 7 |
| Bromus tectorum | 4 | 5 | 7 | 9 | 2 | 4 | 4 | 7 |
| Lolium perenne | 2 | 3 | 4 | 7 | 1 | 1 | 1 | 3 |
| Alopecurus myosuroides | 1 | 2 | 4 | 5 | 1 | 2 | 4 | 4 |
| Digitaria sanguinalis | 1 | 1 | 1 | 1 | 1 | 1 | 1 | 1 |
| Echinochloa crus galli | 1 | 1 | 1 | 5 | 1 | 2 | 2 | 4 |
| Sorghum halepense | 1 | 1 | 1 | 7 | 1 | 2 | 5 | 6 |
| Rottboellia exaltata | 1 | 1 | 3 | 7 | 1 | 1 | 2 | 3 |
| soybean | 7 | 8 | 9 | 9 | 8 | 9 | 9 | 9 |
| cotton | 7 | 8 | 9 | 9 | 4 | 9 | 9 | 9 |
| sunflower | 8 | 9 | 9 | 9 | 7 | 8 | 9 | 9 |
| Abutilon | 1 | 1 | 1 | 3 | 1 | 1 | 2 | 4 |
| Sida spinosa | 1 | 2 | 2 | 2 | 1 | 1 | 2 | 2 |
| Amaranthus retroflexus | 1 | 1 | 1 | 1 | 1 | 1 | 1 | 1 |
| Chenopodium Sp. | 1 | 1 | 1 | 1 | 1 | 1 | 1 | 1 |
| Solanum nigrum | 1 | 1 | 1 | 2 | 1 | 1 | 1 | 1 |
| Stellaria media | 1 | 4 | 6 | 8 | 1 | 1 | 1 | 2 |
| Chrysanthemum leucum | 1 | 1 | 4 | 6 | 1 | 2 | 2 | 4 |
| Galium apanine | 2 | 2 | 2 | 6 | 2 | 3 | 3 | 7 |
| Viola tricolor | 1 | 1 | 1 | 1 | 1 | 1 | 1 | 1 |
| Veronica Sp. | 1 | 1 | 1 | 1 | 1 | 1 | 1 | 1 |

EXAMPLE 18 post-emergence herbicidal action (contact herbicide)

A number of weeds, both monocots and dicots, were sprayed after emergence (at the 4- to 6-leaf stage) with an aqueous dispersion of active ingredient at a rate of 4 kg of active ingredient per hectare and kept at 24°–26° C. and 45–60% relative humidity. 15 days after the treatment, the test is evaluated in accordance with the number scale given above. In this test also, the compounds of Tables 1 to 18 exhibit a pronounced to very pronounced herbicidal action.

EXAMPLE 19

Herbicidal action before emergence of the plants

Plastics pots are filled with expanded vermiculite (density 0.135 g/cm$^3$, water absorption capacity 0.565 liters/liter). After saturating the non-adsorptive vermiculite with an aqueous emulsion of active ingredient in deionised water which contains the active ingredients in a concentration of 70.8 ppm, seeds of the following plants are sown on the surface: *Nasturtium officinalis, Argrostis tenuis, Stellaria media* and *Digitaria sanguinalis*. The test vessels are then kept in a climatic chamber at 20° C., an illumination of about 20 kLux and a relative humidity of 70%. During the germination phase of 4 to 6 days, the pots are covered with transparent material and watered with deionised water to increase the local humidity. After the fifth day, 0.5% of a commercially customary liquid fertiliser ($^R$Greenzit) is added to the water used for watering. 12 days after sowing, the test is evaluated and the condition of the test plants assessed in accordance with the scale given in Example 17.

The results are summarised in the Table below.

| compound no. | application rate | Nasturtium | Agrostis | Stellaria | Digitaria |
|---|---|---|---|---|---|
| 1.27 | 100 ppm | 1 | 1 | 2 | 1 |
| | 10 ppm | 2 | 1 | 2 | 2 |
| 9.27 | 100 ppm | 1 | 1 | 1 | 1 |
| | 10 ppm | 1 | 1 | 2 | 1 |
| 11.27 | 100 ppm | 2 | 2 | 2 | 2 |

EXAMPLE 20

Herbicidal action for paddy

The water weeds *Echinochloa crus galli* and *Monocharia vag.* are sown in plastics beakers (60 cm$^2$ surface area, 500 ml volume). After sowing, the beakers are filled to the soil surface with water. 3 days after sowing, the water level is raised to slightly above (3–5 mm) the surface of the soil. Application is carried out by spraying onto the vessels, 3 days after sowing, using an aqueous emulsion of the test substances. The dose which is therefore used corresponds to a quantity of active ingredient of from 0.5 to 4 kg active ingredient per hectare (spray liquor quantity=550 liters/ha). The plant beakers are then placed in a greenhouse under optimum growth conditions for the rice weeds, i.e. at 25°–30° C. and high humidity. The tests are evaluated 3 weeks after the application. Compounds of Tables 1 to 18 damage the weeds but not the rice.

EXAMPLE 21

Growth inhibition in tropical cover crops

The test plants (*cetrosema plumieri* and *centrosema pubescens*) are raised until fully grown and cut back to a height of 60 cm. After 7 days, the active ingredient is sprayed on in the form of an aqueous emulsion. The test plants are kept at 70% relative humidity and 6000 lux artificial light for 14 hours each day and at a day temperature of 27° and a night temperature of 21° C. 4 weeks after the application, the test is evaluated. In evaluating the test, the new growth is estimated and weighed in comparison with the control and the phytotoxicity is assessed. In this test, the plants treated with the active ingredients of Tables 1 to 18 at application rates of 50–3000 g/ha show a marked reduction in new growth (less than 20% of the new growth in untreated control plants) without the test plants being at the same time damaged.

EXAMPLE 22

Growth regulation in soybeans

Soybeans of the variety "Hark" are sown in plastics containers containing a mixture of soil, peat and sand in a ratio of 6:3:1 and placed in a climatic chamber. By optimum temperature selection, illumination, application of fertiliser and watering, the plants develop after about 5 weeks to the 5 to 6 trifolia leaf stage. At that time, the plants are sprayed until thoroughly wet with an aqueous liquor of an active ingredient of the formula I. The active ingredient concentration is up to 100 g active ingredient/ha. The evaluation is carried out about 5 weeks after application of the active ingredient. In comparison with untreated control plants, the tested active ingredients according to the invention of Tables 1 to 18 cause a marked increase in the number and weight of the pods in the main shoot.

EXAMPLE 23

Growth inhibition in cereals

*Hordeum vulgare* (summer barley) and *Secale* (summer rye) are sown by cereal type in a greenhouse in plastics pots containing sterilised soil and watered as required. About 21 days after sowing, the young shoots are sprayed with an aqueous spray liquor of an active ingredient. The quantity of active ingredient is up to 100 g of active ingredient per hectare. 21 days after the application, the growth of the cereals is assessed. In comparison with untreated controls, the plants treated with active ingredients according to the invention show a reduction in new growth (60–90% of the control) and in some cases an increase in the diameter of the stalk.

EXAMPLE 24

Growth inhibition in grasses

The grasses *Lolium perenne, Poa pratensis, Festuca ovina, Dactylis glomerata* and *Cynodon dactylon* are sown in a greenhouse in plastics trays containing a soil/peat/sand mixture (6:3:1) and watered as required. The emerged grasses are cut back weekly to a height of 4 cm and, about 50 days after sowing and one day after the last cut, sprayed with an aqueous spray liquor of an active ingredient. The quantity of active ingredient is equivalent to up to 500 g of active ingredient per hectare. 21 days after application, the growth of the grasses is assessed.

Tested compounds of Tables 1 to 18 cause a reduction in the new growth of around 10–30% in comparison with the untreated control.

EXAMPLE 25

Desiccating and defoliating action

Cotton plants of the variety Deltapine were raised in clay pots in a greenhouse. When the capsule formation had been completed, they were sprayed with aqueous preparations of an active ingredient at an application rate corresponding to 1.2, 0.6 and 0.3 kg/ha in the field. Untreated plants were left as a control. The test was evaluated 3, 7 and 14 days after application of the active ingredient by determining the degree of defoliation (% fallen leaves) and the degree of desiccation (% desiccation of the leaves remaining on the plants).

In this test, on the plants sprayed with compounds of Tables 1 to 18 at application rates of 0.6 and 1.2 kg/ha, only a few dried leaves still remained on the plants after 7 days (>80% leaf fall and desiccation).

We claim:

1. N-phenylmaleic acid imides of the formula I $$\begin{array}{c} \text{Y} \\ \text{Z} \end{array} \begin{array}{c} \text{O} \\ \parallel \\ \text{C} \\ \text{N} \\ \text{C} \\ \parallel \\ \text{O} \end{array} \begin{array}{c} \text{R}^1 \\ \text{R}^2 \\ \text{A} \end{array} \quad (I)$$

in which
R$^1$ represents hydrogen or fluorine,
R$^2$ represents halogen,
Y represents C$_1$–C$_8$-alkyl,
Z represents hydrogen or C$_1$–C$_8$-alkyl, and
A represents hydrogen or a group $$-\underset{\underset{O}{\parallel}}{C}-R^3, \ -\underset{\underset{O}{\parallel}}{C}-R^7 \text{ or } -X-R^8,$$

wherein
R$^3$ represents hydrogen, C$_1$–C$_4$-alkyl or C$_1$–C$_4$-haloalkyl,
R$^7$ represents hydroxy, C$_1$–C$_8$-alkoxy, C$_2$–C$_8$alkoxyalkoxy, C$_2$–C$_8$-alkylthioalkoxy, C$_3$–C$_8$-alkenyloxy, C$_2$–C$_8$-haloalkenyloxy, C$_3$–C$_8$-alkynyloxy, C$_3$–C$_7$-cycloalkoxy, C$_1$–C$_8$-alkythio, C$_3$–C$_8$-alkenylthio, or C$_1$–C$_4$-alkylthio substituted by C$_1$–C$_8$-alkoxycarbonyl, C$_2$–C$_8$-alkynyloxycarbonyl, C$_1$–C$_8$-alkylthiocarbonyl, C$_3$–C$_8$-alkenylthiocarbonyl or by C$_3$–C$_8$-alkynylthiocarbonyl; or C$_1$–C$_4$-alkoxy substituted by C$_1$–C$_8$-alkoxycarbonyl, C$_2$–C$_8$-alkoxyalkoxycarbonyl, C$_3$–C$_8$-alkenyloxycarbonyl, C$_3$–C$_8$-alkynloxycarbonyl, C$_1$–C$_8$-alkylthiocarbonyl, C$_3$–C$_8$-alkenylthiocarbonyl, C$_3$–C$_8$-alkynyltiocarbonyl,
R$^8$ represents C$_1$–C$_8$-alkyl, C$_2$–C$_8$-alkoxyalkyl, C$_2$–C$_8$-alkylthioalkyl, C$_2$–C$_8$-haloalkyl, C$_3$–C$_8$-alkenyl, C$_3$–C$_8$-haloalkenyl, C$_3$–C$_8$-alkynyl, C$_3$–C$_7$-cycloalkyl, C$_1$–C$_8$-alkylcarbonyl, allylcarbonyl, phenyl, halophenyl, C$_1$–C$_4$-alkylphenyl, C$_1$–C$_4$-alkoxyphenyl, C$_1$–C$_4$-haloalkylphenyl, C$_1$–C$_4$-haloalkoxyphenyl, nitrophenyl, cyanophenyl, C$_1$–C$_8$-alkoxycarbonyl, C$_2$–C$_8$-alkoxyalkoxycarbonyl, C$_3$–C$_8$-akoxycarbonyl, C$_2$–C$_8$-alkoxyalkoxycarbonyl, C$_3$–C$_8$-alkenyloxycarbonyl, C$_3$–C$_8$-alkynyloxycarbonyl, C$_1$–C$_8$-alkyl-thiocarbonyl, C$_3$–C$_8$-alkenylthiocarbonyl or C$_3$–C$_8$alkynylthiocarbonyl.

2. A-N-phenylmaleic acid imide according to claim 1 in which
R$_1$ represents hydrogen or fluorine,
R$_2$ represents chlorine or bromine,
Y represents C$_1$–C$_8$ alkyl,
Z represents hydrogen or C$_1$–C$_8$ alkyl,
A represents the radical —XR$^8$ and X and $R^8$ are as defined in claim 1.

3. Compounds according to claim 1, in which
$R^1$ represents hydrogen or fluorine,
$R^2$ represents chlorine or bromine,
Y represents $C_1$-$C_8$-alkyl,
Z represents hydrogen or $C_1$-$C_8$-alkyl,
A represents the radical —$COR^3$, and
$R^3$ represents hydrogen, $C_1$-$C_4$-alkyl or $C_1$-$C_4$-haloalkyl.

4. Compounds according to claim 1, in which
$R^1$ represents hydrogen or fluorine,
$R^2$ represents chlorine or bromine,
Y represents $C_1$-$C_8$-alkyl,
Z represents hydrogen or $C_1$-$C_8$-alkyl,
A represents the radical —$COR^7$, and
$R^7$ is as defined in claim 1.

5. N-(4-chloro-2-fluoro-5-isopropoxyphenyl)-2,3-dimethylmaleic acid imide according to claim 1.

6. N-(4-chloro-2-fluoro-5-isopropoxyphenyl)-2-n-butyl-3-methyl-maleic acid imide according to claim 1.

7. N-(4-chloro-2-fluoro-5-isopropoxyphenyl)-3-methyl-2-ethyl-maleic acid imide according to claim 1.

8. N-(4-chloro-2-fluoro-5-isopropoxyphenyl)-2-ehtyl-3-methyl-maleic acid imide according to claim 1.

9. N-(4-chloro-2-fluoro-5-isopropoxycarbonylphenyl)-2,3-dimethylmaleic acid imide according to claim 1.

10. Compounds according to claim 1, in which
$R^1$ represents hydrogen or fluorine,
$R^2$ represents chlorine or bromine,
Y and Z each represents methyl, and
A has one of the meanings given in claim 1.

11. Compounds according to claim 1, in which
$R^1$ represents hydrogen or fluorine,
$R^2$ represents chlorine or bromine,
Y represents ethyl,
Z represents methyl, and
A has one of the meanings given in claim 1.

12. Compounds according to claim 1, in which
$R^1$ represents hydrogen or fluorine,
$R^2$ represents chlorine or bromine,
Y represents isopropyl,
Z represents methyl, and
A has one of the meanings given in claim 1.

13. Compounds according to claim 1, in which
$R^1$ represents hydrogen or fluorine,
$R^2$ represents chlorine or bromine,
Y represents isopropyl,
Z represents hydrogen, and
A has one of the meanings given in claim 1.

14. Compounds according to claim 1, in which
$R^1$ represents hydrogen or fluorine,
$R^2$ represents chlorine or bromine,
Y represents n-butyl,
Z represents methyl, and
A has one of the meanings given in claim 1.

15. A herbicidal and plant growth regulating composition, which contains a herbicidally and growth regulating effective amount of an N-phenylmaleic acid imide according to claim 1, together with inert carriers or other additives.

16. A method for inhibiting the growth of useful plants, which comprises treating the plants with an effective amount of an ingredient according to claim 1 or of a composition containing such an active ingredient.

17. A method of controlling weeds, which comprises treating the weeds or their environment with an effective amount of a compound according to claim 1 or of a composition containing such a compound.

18. A method according to claim 7 of selectively controlling weeds in crops of soybeans, cotton, oats, rye, millet, maize, wheat, barley and rice.

* * * * *